(12) United States Patent
Izume et al.

(10) Patent No.: US 11,680,953 B2
(45) Date of Patent: Jun. 20, 2023

(54) CELL TRANSFER DEVICE AND CELL TRANSFER METHOD

(71) Applicant: YAMAHA HATSUDOKI KABUSHIKI KAISHA, Iwata (JP)

(72) Inventors: Yohei Izume, Shizuoka (JP); Masaru Sakamoto, Shizuoka (JP)

(73) Assignee: YAMAHA HATSUDOKI KABUSHIKI KAISHA, Iwata (JP)

( * ) Notice: Subject to any disclaimer, the term of this patent is extended or adjusted under 35 U.S.C. 154(b) by 841 days.

(21) Appl. No.: 16/500,159

(22) PCT Filed: Feb. 26, 2018

(86) PCT No.: PCT/JP2018/006972
§ 371 (c)(1),
(2) Date: Oct. 2, 2019

(87) PCT Pub. No.: WO2018/193719
PCT Pub. Date: Oct. 25, 2018

(65) Prior Publication Data
US 2020/0355717 A1 Nov. 12, 2020

(30) Foreign Application Priority Data
Apr. 20, 2017 (JP) .............................. JP2017-083909

(51) Int. Cl.
B01L 3/00 (2006.01)
G01N 35/10 (2006.01)
B01L 3/02 (2006.01)

(52) U.S. Cl.
CPC ........ G01N 35/1065 (2013.01); B01L 3/0227 (2013.01); B01L 3/5085 (2013.01);
(Continued)

(58) Field of Classification Search
CPC . B01L 3/0227; B01L 3/5085; B01L 2200/025
(Continued)

(56) References Cited

U.S. PATENT DOCUMENTS

2007/0264725 A1 11/2007 Wiggli et al.
2010/0179687 A1 7/2010 Wiggli et al.
(Continued)

FOREIGN PATENT DOCUMENTS

JP 2005-221469 A 8/2005
JP 4616342 B2 1/2011
(Continued)

OTHER PUBLICATIONS

An Office Action mailed by China National Intellectual Property Administration dated Jul. 20, 2022, which corresponds to Chinese Patent Application No. 201880025207.0 and is related to U.S. Appl. No. 16/500,159; with English language translation.
(Continued)

Primary Examiner — Natalia Levkovich
(74) Attorney, Agent, or Firm — Studebaker & Brackett PC

(57) ABSTRACT

The cell transfer device includes a head group including a plurality of heads to which tips are attached and which move along a first direction; a head unit in which the head group is installed and which moves in a second direction and in a third direction; and a plurality of drive motors which are mounted on the head unit and which generate driving force to cause the head to move along the first direction. The plurality of drive motors are separately arranged on one side and the other side in the third direction with the head group provided therebetween. The head group includes a first head and a second head. The first head is driven by the drive motor arranged on the one side in the third direction, and the
(Continued)

second head is driven by the drive motor arranged on the other side in the third direction.

7 Claims, 15 Drawing Sheets

(52) U.S. Cl.
CPC ... *B01L 2200/025* (2013.01); *B01L 2200/143* (2013.01); *B01L 2400/0478* (2013.01); *G01N 2035/1034* (2013.01)

(58) Field of Classification Search
USPC .................................................. 522/521, 504
See application file for complete search history.

(56) References Cited

U.S. PATENT DOCUMENTS

| | | |
|---|---|---|
| 2012/0028240 A1 | 2/2012 | Richmond et al. |
| 2014/0030166 A1* | 1/2014 | Douglas ............... B01L 3/0227 422/507 |
| 2017/0123932 A1 | 5/2017 | Ito et al. |
| 2017/0131308 A1 | 5/2017 | Ito et al. |
| 2017/0131315 A1 | 5/2017 | Ito et al. |
| 2017/0167955 A1 | 6/2017 | Ito et al. |

FOREIGN PATENT DOCUMENTS

| | | |
|---|---|---|
| WO | 03035260 A1 | 5/2003 |
| WO | 2015/193970 A1 | 12/2015 |

OTHER PUBLICATIONS

The extended European search report issued by the European Patent Office dated Feb. 12, 2020, which corresponds to European Patent Application No. 18787426.8-1101 and is related to U.S. Appl. No. 16/500,159.

International Search Report issued in PCT/JP2018/006972; dated May 22, 2018.

* cited by examiner

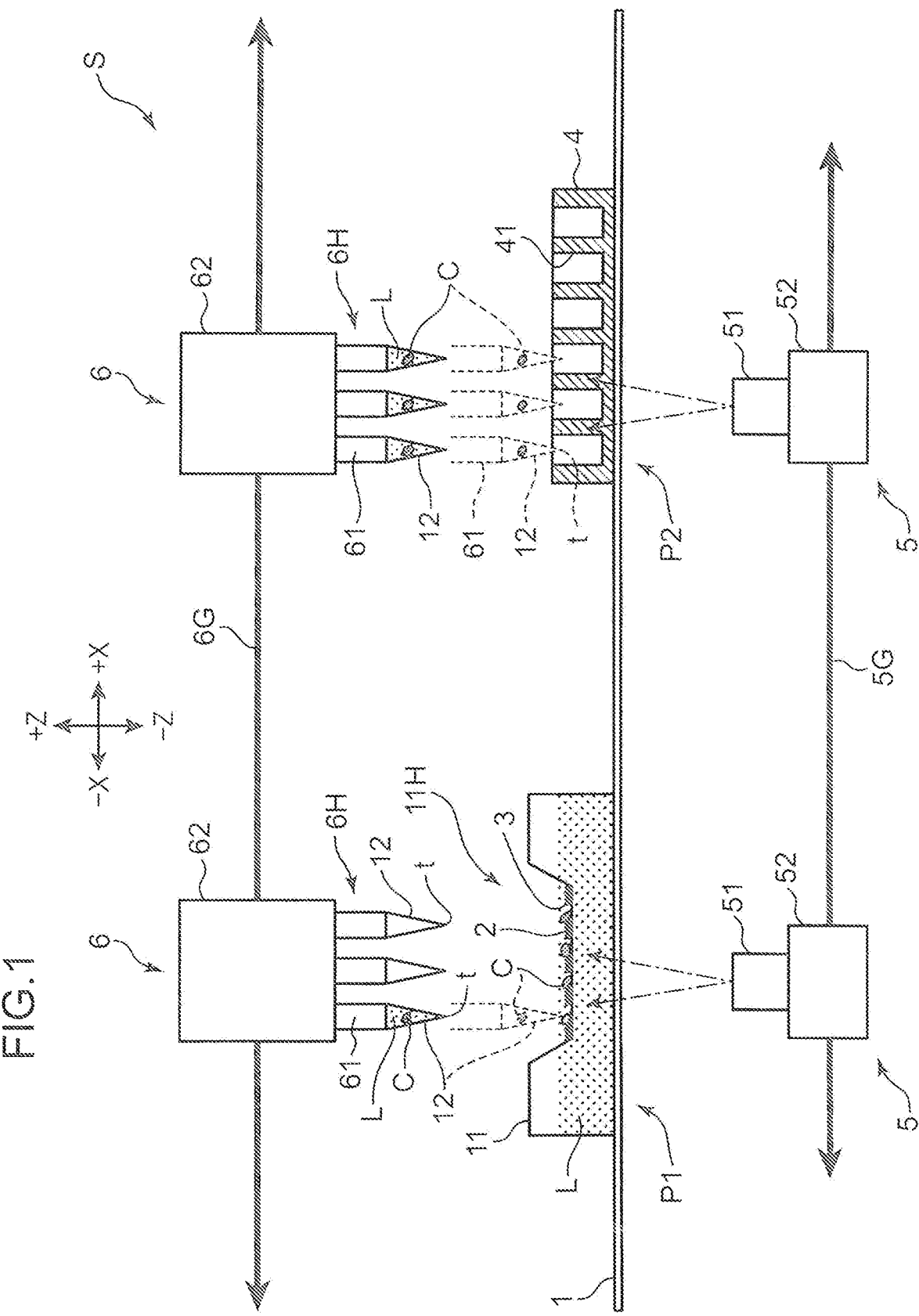

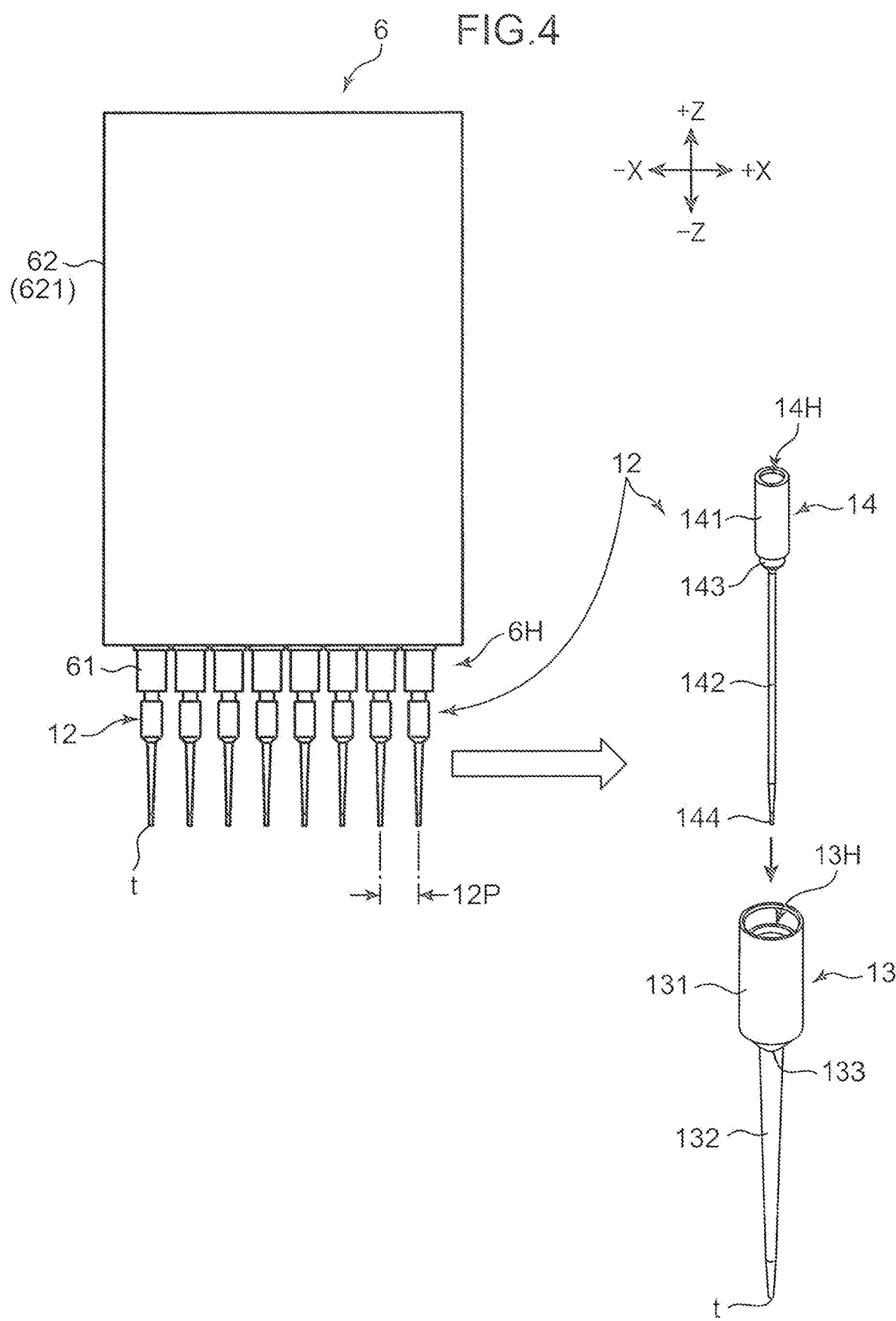

CELL TRANSFER DEVICE AND CELL TRANSFER METHOD

CROSS-REFERENCE TO RELATED APPLICATIONS

This application is a National Stage of International Patent Application No. PCT/JP2018/006972, filed Feb. 26, 2018, which claims benefit from JP 2017-083909, filed Apr. 20, 2017, the entire content of each are incorporated herein by reference.

BACKGROUND

Technical Field

The present disclosure relates to a cell transfer device which moves a tip having suctioned a cell to a predetermined position and then causes the tip to discharge the cell, and a transfer method therefor.

Background Art

For example, in applications for medical or biological research, there is a case where a single cell, or a cellular aggregate which is a result of three-dimensional agglomeration of cells, or a cell mass obtained by agglomerating and culturing a piece of a cell (hereinafter, simply referred to as a cell in the present specification) is stored in a well of a microplate having wells aligned in a matrix for the purpose of processing work such as observation, checking of efficacy of medicines, examination, or culture. A cell to be stored in the well is selected on a dish having a holding recess which can store a cell. The selected cells are suctioned from the holding recess by a plurality of tips attached to a plurality of heads movable up and down and capable of generating a negative pressure, and transferred to arrangement positions in the microplate. After the transfer, the cells suctioned by the tips are discharged to the wells of the microplate.

Individual discharging of a cell from each of the plurality of tips to each well has low work efficiency in cell transfer work. Accordingly, it is preferable to simultaneously discharge cells from the plurality of tips to the wells. For example, Japanese Patent No. 4616342 discloses matching an arrangement pitch of a dispenser tip with an arrangement pitch of a well. The matching enables execution of the simultaneous discharge.

There is a case, however, where it is difficult to match an alignment pitch of the heads to which the tips are attached with an alignment pitch of the wells of the microplate. In a case, for example, of a standard microplate having 24×16 wells, the alignment pitch of the well is 4.5 mm On the other hand, it is necessary to install, in the head, a drive motor which causes the head to be raised and lowered, and further a suction motor for causing the head to generate the negative pressure, and the like. However, the motor capable of generating a required driving force generally becomes larger in size than the alignment pitch of the well. Such a condition of a head configuration involves a problem that execution of the simultaneous discharge is difficult.

SUMMARY

Accordingly, the present disclosure provides a cell transfer device in which a tip attached to a head mounted with a drive motor can be aligned at a required pitch, and a cell transfer method using the cell transfer device.

A cell transfer device according to one aspect of the present disclosure includes a head group including a plurality of heads to which tips for suctioning and discharging cells are attached and which are capable of moving along a first direction; a head unit in which the head group is installed and which is capable of moving in a second direction orthogonal to the first direction and in a third direction orthogonal to both the first direction and the second direction; and a plurality of drive motors which are mounted on the head unit so as to each correspond to each of the heads and which generate driving force to cause the head to move along the first direction. The plurality of drive motors are separately arranged on one side and the other side in the third direction with the head group provided therebetween in a plan view from the first direction, and the head group includes at least a first head and a second head adjacent to the first head in the second direction. The first head is driven by the drive motor arranged on the one side in the third direction. The second head is driven by the drive motor arranged on the other side in the third direction.

A cell transfer method according to another aspect of the present disclosure is a cell transfer method of transferring a cell suctioned by a tip to a predetermined position and discharging the cell, the method including the steps of preparing a microplate including a plurality of wells to which the cells are discharged, the wells being aligned at a first pitch in a predetermined direction, and the cell transfer device in which a plurality of heads are aligned such that the tip is aligned at a second pitch that is n-times the first pitch (n is an integer of 1 or more); mounting the microplate in a movable range of the head unit; moving the head unit to a mounting position of the microplate in a state where the cell is being suctioned by the tip of the head group; and simultaneously driving the plurality of drive motors to simultaneously move the plurality of heads in the first direction such that distal end openings of the plurality of tips enter the respective wells, and causing the plurality of tips to simultaneously discharge the cells.

BRIEF DESCRIPTION OF THE DRAWING

FIG. 1 is a view schematically showing a cell transfer device according to an embodiment of the present disclosure;

FIG. 4 is a front view showing one example of a head unit together with an exploded perspective view of tips to be attached to heads;

DETAILED DESCRIPTION

Figure 2A:
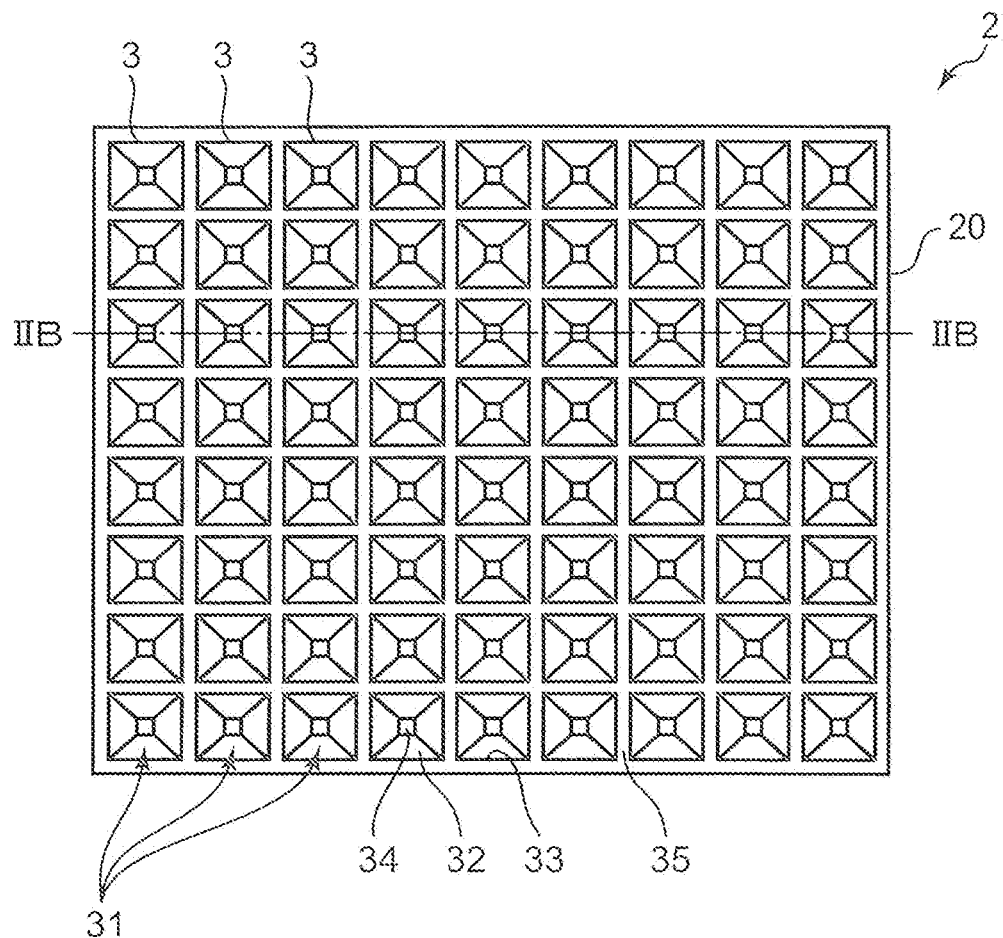
FIG. 2A is a top view of a dish provided in a selection container for use in the cell transfer device.

In the following, embodiments of the present disclosure will be described in detail with reference to the drawings. In a cell transfer device according to the present disclosure, a tissue-derived cell, a cell mass, a cellular aggregate (spheroid) or the like is used as a transfer target. For example, a tissue-derived cellular aggregate is formed by agglomerating several to several hundred thousands of cells. Therefore, a cellular aggregate varies in size. Although a cellular aggregate formed by a living cell is generally spherical, when a part of a cell constituting the cellular aggregate deteriorates or becomes a dead cell, the cellular aggregate may have a distorted shape or have uneven density in some cases. In a test for a biology-related technique or in a medical field, a cell transfer device is used which picks a usable cellular aggregate by a tip from among a plurality of cellular aggregates having various shapes which are carried by dishes on a selection stage, and transfers the picked cellular aggregate to a microplate. On the microplate, various processing is executed for the cellular aggregate, such as observation, checking of efficacy of medicines, examination, and culture. In the following description, in view of including such a cellular aggregate as described above, the cellular aggregate will be expressed simply as a cell C.

Overall Configuration of Cell Transfer Device

FIG. 1 is a view schematically showing an overall configuration of a cell transfer device S of the present embodiment. Here, the cell transfer device S which transfers a cell C between two containers is illustrated. FIG. 1 and other figures have indications of an X direction, a Y direction and a Z direction. For example, the X direction represents a right-left direction, the Y direction represents a front-rear direction, and the Z direction represents an up-down direction, in which +X represents right, −X left, +Y front, −Y rear, +Z up, and −Z down. Hereinafter, description will be made based on indication of XYZ directions or on the above example of right and left, front and rear, and up and down according to conditions.

The cell transfer device S includes a light transmissive base 1 having a level mounting surface (an upper surface), a camera unit 5 arranged below the base 1, and a head unit 6 arranged above the base 1. At a first mounting position P1 of the base 1, a selection container 11 provided with a dish 2 is mounted and at a second mounting position P2, a microplate 4 is mounted. The head unit 6 includes a head group 6H having a plurality of heads 61 movable in the Z direction (a first direction), to which tips 12 for suctioning and discharging the cell C are attached. The camera unit 5 and the head unit 6 are movable in the X direction (a second direction orthogonal to the first direction) and the Y direction (a third direction orthogonal to both the first direction and the second direction). The dish 2 and the microplate 4 are mounted on the upper surface of the base 1 within a movable range of the head unit 6.

Roughly explained, the cell transfer device S is a device which individually suctions the cell C by each of the plurality of tips 12 from the dish 2 of the selection container 11 which holds numerous cells C, and transfers the cells C to the microplate 4, and also simultaneously discharges the cells C from the plurality of tips 12 to the microplate 4 (wells 41). Each portion of the cell transfer device S will be described in the following.

The base 1 is a rectangular flat plate having predetermined rigidity and a part or all of the base 1 is formed with a light transmissive material. The base 1 is preferably a glass plate. Forming the base 1 with a light transmissive material such as a glass plate allows the camera unit 5 arranged below the base 1 to capture the image of the selection container 11 (the dish 2) and the microplate 4 arranged on the upper surface of the base 1 through the base 1.

The selection container 11 is a container as a transfer source of the cell C, and accumulates a culture medium L and holds the cell selection dish 2 being immersed in the culture medium L. The dish 2 is a plate which holds the cell C and has, on its upper surface, holding recesses 3 (holding portions) capable of individually storing and holding the cells C. The culture medium L is not particularly limited as long as it does not deteriorate properties of the cell C, and can be appropriately selected according to a kind of the cell C.

The selection container 11 is provided, on its upper surface side, with a rectangular upper opening 11H. The upper opening 11H is an opening for inserting the cell C and picking the selected cell C. The dish 2 is arranged below the upper opening 11H. The selection container 11 and the dish 2 for use are made of a light transmissive resin material or glass. This is for enabling the camera unit 5 arranged below the selection container 11 to observe the cell C carried on the dish 2.

The plurality of cells C being dispersed in a cell culture solution are injected to the selection container 11 from the dispensation tip (not shown). The dispensation tip suctions, from the container which accumulates a cell culture solution containing a large number of the cells C, the cell culture solution together with the cells C and holds the solution and the cells in the dispensation tip. Thereafter, the dispensation tip is moved to a position above the selection container 11 to access the upper surface of the dish 2 through the upper opening 11H. Then, with a distal end opening of the dispensation tip immersed in the culture medium L of the selection container 11, the cell C held in the dispensation tip is discharged on the dish 2 together with the cell culture solution.

Details of Dish

Figure 2B:
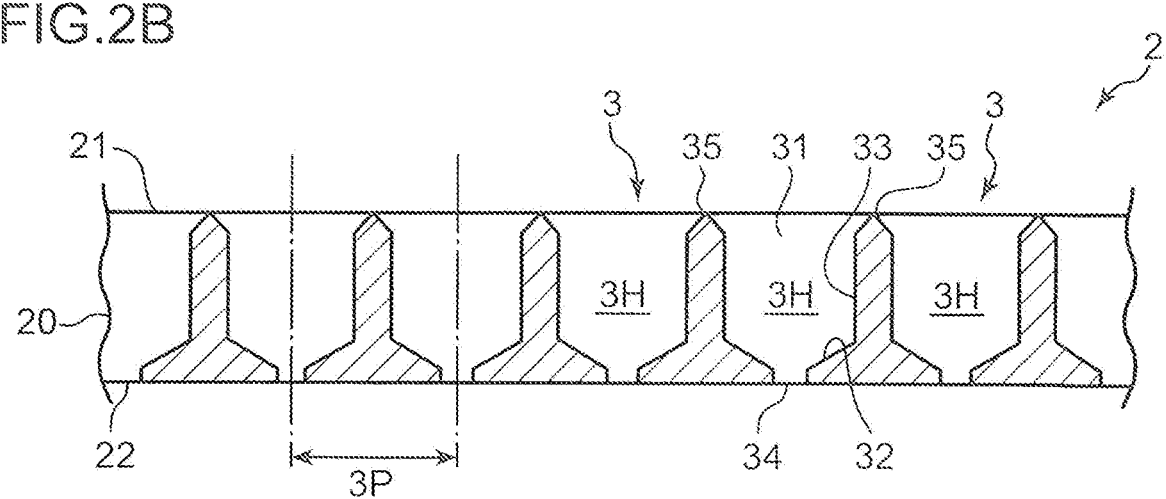
FIG. 2B is a sectional view taken along line IIB-IIB in FIG. 2A.

Detailed structure of the dish 2 will be described. FIG. 2A is a top view of the dish 2, and FIG. 2B is a sectional view take along line IIB-IIB in FIG. 2A. The dish 2 is provided with a dish main body 20 and a plurality of holding recesses 3 formed in the dish main body 20. The dish main body 20 is made of a flat plate-shaped member having a predetermined thickness and has an upper surface 21 and a lower surface 22. The holding recess 3 has a reception opening (opening portion 31) for the cell C on the side of the upper surface 21. The dish 2 is immersed in the culture medium L in the selection container 11. Specifically, while the upper surface 21 of the dish main body 20 is immersed in the culture medium L in the selection container 11, the lower surface 22 is held in the selection container 11 in a state of being spaced from a bottom plate of the selection container 11 (see FIG. 1).

Each of the holding recesses 3 includes the opening portion 31, a bottom portion 32, a tubular wall surface 33, a hole portion 34 and a boundary portion 35. In the present embodiment, there is shown an example where the holding recesses 3 which are square in a top view are aligned in a matrix. As shown in FIG. 2B, the plurality of holding recesses 3 are aligned at a predetermined recess alignment pitch 3P (third pitch). The recess alignment pitch 3P is a pitch narrower than an alignment pitch of the head 61 (the tip 12) to be described later and narrower than an alignment pitch of the well 41 of the microplate 4.

The opening portion 31 is a square opening provided in the upper surface 21 and has a size which allows a distal end opening portion t of the tip 12 for selection to enter. The bottom portion 32 is positioned within the dish main body 20 and near the lower surface 22. The bottom portion 32 is an inclined surface gradually slanting toward the center (the center of the square). The tubular wall surface 33 is a wall surface extending vertically downward from the opening portion 31 toward the bottom portion 32. The hole portion 34 is a through-hole vertically penetrating between the center of the bottom portion 32 and the lower surface 22. The boundary portion 35 is a portion positioned in the upper surface 21 and corresponding to an opening edge of each holding recess 3 and is a ridgeline that partitions the holding recesses 3.

The bottom portion 32 and the tubular wall surface 33 of each holding recess 3 partition a storage space 3H which stores the cell C. The storage space 3H is in general intended to store one cell C. The hole portion 34 is provided for causing small cells and impurities of a size other than a desired size to escape from the storage space 3H. Accordingly, the hole portion 34 has a size selected to prevent the cell C of a desired size from passing through but allow small cells and impurities of a size other than the desired size to pass through. In this manner, the cell C to be selected is trapped in the holding recess 3, while impurities and the like drop from the hole portion 34 to the bottom plate of the selection container 18.

Details of Microplate

Returning to FIG. 1, the microplate 4 is a container which becomes a transfer destination of the cell C and has a plurality of wells 41 to which the cells C are discharged. The well 41 is a bottomed hole which is opened in an upper surface of the microplate 4. In one well 41, a necessary number (ordinarily one) of the cells C are stored together with the culture medium L. The microplate 4 used here is also made of a light transmissive resin material or glass. This is for enabling the cell C carried in the well 41 to be observed by the camera unit 5 arranged below the microplate 4.

Figure 3A:
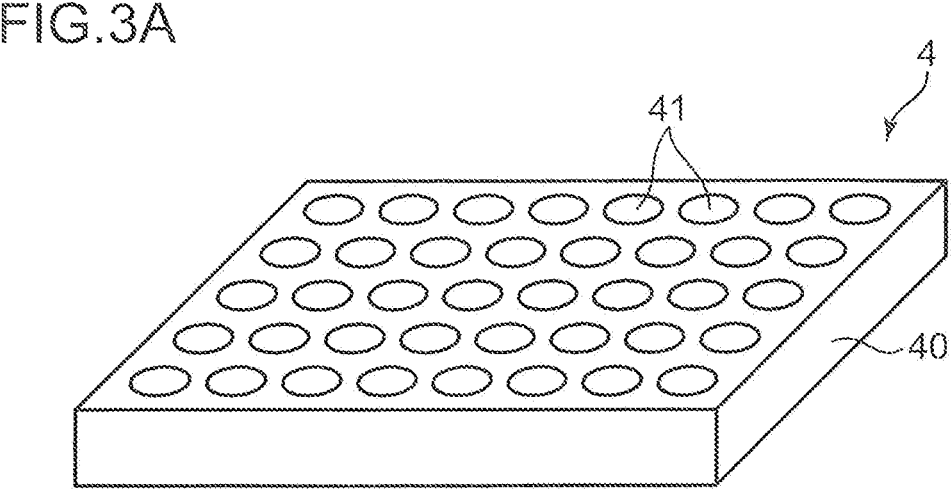
FIG. 3A is a perspective view of a microplate for use in the cell transfer device and FIG. 3B is a sectional view of the microplate having 384 wells.

FIG. 3A is a perspective view showing one example of the microplate 4. The microplate 4 includes a plate main body 40 and the plurality of wells 41 aligned in the plate main body 40 in a matrix. Since the distal end opening portion t of the tip 12 enters the well 41 during discharge of the cell C, each well 41 has an opening diameter which allows the tip 12 to enter with a margin.

Commercially available microplates have a standard size. A standard microplate has a predetermined length-to-width size (length 85.48 mm×width 127.76 mm) and has a predetermined number of wells (see e.g., "Footprint Dimensionsfor Microplates" defined by SLAS (Society for Laboratory Automation and Screening) of ANSI (American National Standards Institute) in 2004). A general number of wells is 24×16 (384 wells), the wells being aligned at a predetermined pitch in a matrix.

Figure 3B:
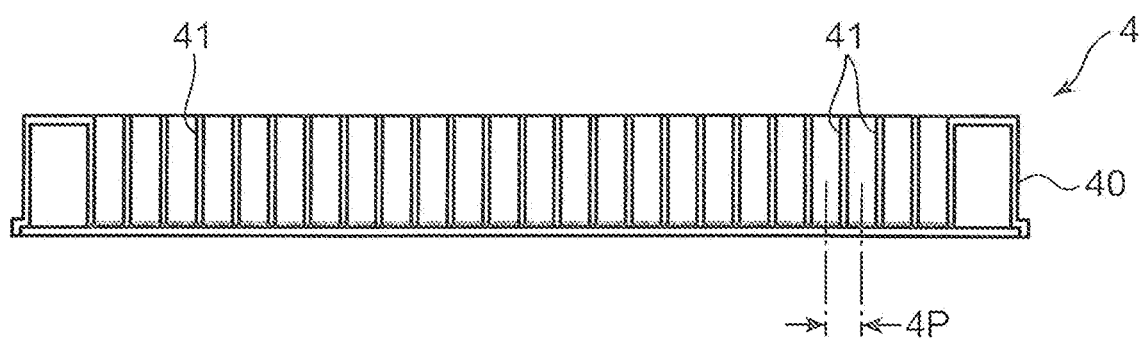

FIG. 3B is a sectional view of the microplate 4 with 384 wells. As shown in the figure, 24 wells 41 are aligned at an equal well pitch 4P in a longitudinal direction of the microplate 4 (16 in a shorter side direction). In a case of 384 wells, the well pitch 4P is 4.5 mm. A general-purpose microplate 4 includes 1536 wells and 96 wells other than 384 wells. In a case of 1536 wells, the well pitch 4P is 2.25 mm, and in a case of 96 wells, the well pitch 4P is 9.0 mm. In other words, any of the microplates 4 has a well pitch 4P of a multiple of 2.25 mm.

Camera Unit

The camera unit 5, which captures an image of the cell C held in the selection container 11 or the microplate 4 from their lower sides, is provided with a lens unit 51 and a camera main body 52. The lens unit 51 is an objective lens for use in an optical microscope and includes a lens group which forms an optical image of a predetermined magnification, and a lens barrel which houses the lens group. The camera main body 52 is provided with an imaging element such as a CCD image sensor. The lens unit 51 forms an optical image of an imaging target on a light receiving surface of the imaging element. The camera unit 5 is movable along a guide rail 5G extending in the right-left direction in parallel with the base 1, under the base 1 and in the X direction. Although not illustrated in FIG. 1, the camera unit 5 is movable also in the Y direction. The lens unit 51 is movable in the Z direction for focusing operation.

Head Unit

The head unit 6 is provided for transferring the cell C from the dish 2 to the microplate 4 and includes the head group 6H including the plurality of heads 61, and a head main body 62 in which the head group 6H is installed. The tip 12 which conducts suctioning and discharging of the cell C is attached to a distal end of each head 61. The head main body 62 holds the head 61 so as to be raised and lowered in +Z and -Z directions and is movable along a guide rail 6G in +X and -X directions. Although not illustrated in FIG. 1, the head main body 62 is movable also in the Y direction.

FIG. 4 is a front view showing one example of the head unit 6 together with an exploded perspective view of the tips 12 to be attached to the head 61. The head unit 6 includes a head cover 621 covering a mechanism part of the head main body 62. The head group 6H is exposed downward from a lower end side (the -Z side) of the head cover 621. FIG. 4 illustrates the head group 6H including eight heads 61 linearly aligned in the X direction.

The tip 12 attached to each head 61 includes a syringe 13 internally provided with a tubular passage serving as a suction route of the cell C, and a plunger 14 which reciprocates in the tubular passage while being in sliding contact with an inner circumferential wall of the syringe 13. The syringe 13 includes a syringe base end portion 131 which is configured by a large-diameter cylindrical body, a syringe main body 132 which is configured by an elongated small-diameter cylindrical body, and a tapered cylinder portion 133 which connects the base end portion 131 and the main body 132 to each other. The tubular passage is formed in the syringe main body 132. The above distal end opening portion t is provided at a distal end of the syringe main body 132. The plunger 14 includes a plunger base end portion 141 configured by a cylindrical body, a needle-like plunger main body 142, and a tapered portion 143 which connects the base end portion 141 and the main body 142.

The syringe base end portion 131 includes a cylindrical hollow portion 14H. The plunger base end portion 141 has a size which allows the plunger base end portion 141 to be housed in the hollow portion 14H. The plunger main body 142 has an outer diameter set to be slightly smaller than an inner diameter of the tubular passage. The tapered cylinder portion 133 has an inner circumferential surface with a shape coincident with a curved surface shape of an outer circumferential surface of the tapered portion 143. The plunger 14 is installed in the syringe 13 such that the plunger base end portion 141 is housed in the hollow portion 14H and the plunger main body 142 is inserted in the tubular passage of the syringe main body 132. In a state where the plunger 14 is inserted most deeply into the syringe 13, a distal end portion 144 of the plunger 14 slightly protrudes from the distal end opening portion t.

Movement of the plunger 14 to the +Z side with respect to the syringe 13 generates suction force at the distal end opening portion t. On the other hand, movement of the plunger 14 to the −Z side generates discharge force at the distal end opening portion t. These suction force and discharge force enable suction of the cell C from the distal end opening portion t and discharge of the suctioned cell C from the distal end opening portion t.

The head main body 62 includes a piston mechanism (a suction motor 82 to be described later is a drive source) which causes the piston rod to be raised and lowered in the Z direction within the tubular rod in addition to a raising and lowering mechanism (a drive motor 81 to be described later is a drive source) which causes the head 61 itself to be raised and lowered in the Z direction. Movement of the plunger 14 relative to the syringe 13 in the Z direction by the piston mechanism causes the suction force and the discharge force to be applied to the distal end opening portion t to the tip 12. A structure of the head 61 will be detailed later.

The plurality of tips 12 attached to the plurality of heads 61, respectively, are aligned in the X direction at a predetermined tip alignment pitch 12P (a second pitch). The tip alignment pitch 12P is n-times (n is an integer of 1 or more) the well pitch 4P (a first pitch) of the wells 41 in the microplate 4. For example, in the case of the microplate 4 having 384 wells, since the well pitch 4P is 4.5 mm as described above, the tip alignment pitch 12P can be set to 4.5 mm×2=9.0 mm. The plurality of heads 61 are aligned in the head main body 62 such that the plurality of tips 12 are aligned at such tip alignment pitch 12P.

Figure 5:
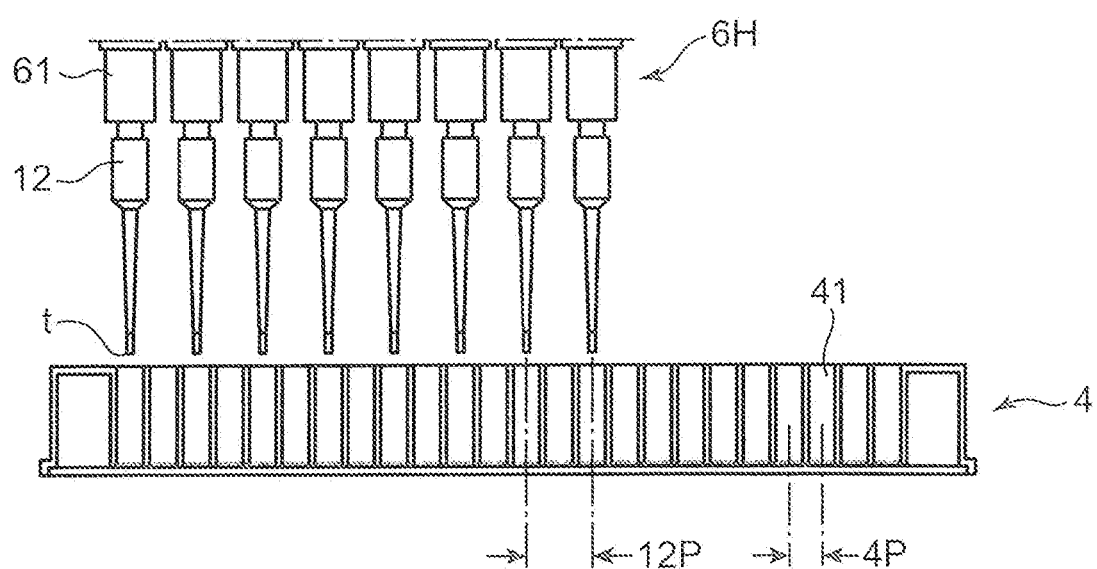
FIG. 5 is a view for explaining simultaneous discharge of cells from the plurality of tips to the wells of the microplate.

Setting the well pitch 4P and the tip alignment pitch 12P to have such a relation as described above enables the plurality of tips 12 to simultaneously access the plurality of wells 41 and simultaneously discharge the cell C. FIG. 5 shows an access status of the tip 12 to the well 41 in a case where the tip alignment pitch 12P is set to be two times the well pitch 4P. In this case, a group of the eight tips 12 is opposed to an alignment region of the 16 wells 41 and the tips 12 are opposed to every other well, i.e., the eight wells 41. Accordingly, lowering the head group 6H in the state shown in FIG. 5 enables the distal end opening portion t of each tip 12 to enter a cavity of each well 41, thereby causing simultaneous discharge operation of the cell C to be executed.

The recess alignment pitch 3P (the third pitch) of the holding recess 3 in the dish 2 shown in FIG. 2B is set to be a considerably narrower pitch than the well pitch 4P. In other words, the dish 2 has a size quite smaller than a size of the head 61 and therefore, it is difficult to produce the head group 6H according to the recess alignment pitch 3P. Accordingly, simultaneous suction of the cells C using the plurality of tips 12 is difficult for the dish 2.

Description of Cell Transfer Method

Subsequently, a cell transfer method according to an embodiment of the present disclosure will be described with reference to FIG. 1. First, a step of preparing a necessary facility is executed. The above-described cell transfer device S is prepared upon execution of the cell transfer method. Specifically, there are prepared the microplate 4 in which the plurality of wells 41 to which the cells C are discharged are linearly aligned at the predetermined well pitch 4P, the selection container 11 holding the dish 2 having the holding recesses 3 which hold the cells, and the head unit 6 in which the plurality of heads 61 are aligned such that the tips 12 are aligned at the tip alignment pitch 12P that is n-times the well pitch 4P.

Subsequently, on the upper surface of the base 1 within a movable range of the head unit 6, and within a movable range of the camera unit 5, the selection container 11 and the microplate 4 are mounted (a mounting step). Thereafter, the plurality of cells C being dispersed in a cell culture solution are injected to the selection container 11 from the dispensation tip (not shown). In other words, the cells C are scattered on the dish 2. Then, the camera unit 5 is moved to a position below the selection container 11 along the guide rail 5G to capture an image of the cell C carried on the dish 2, as well as making determination for selecting a cell C to be transferred (good cell C).

Thereafter, a step of moving the head unit 6 is executed. Here, each tip 12 attached to each head 61 of the head group 6H is in an empty state (a state of suctioning nothing) and the head unit 6 is moved along the guide rail 6G to a mounting position of the selection container 11 which holds the dish 2.

Next, a step of causing the cell C to be suctioned by the tip 12 is executed. The cells C selected in the preceding step as a transfer target are suctioned, and coordinate information indicative of carriage positions of these cells C is given to a controller of the head unit 6. In the suction step, the heads 61 (the tips 12) are lowered one by one. Specifically, one head 61 is moved downward (the −Z direction) by driving the raising and lowering mechanism (the drive motor 81 to be described later) of one head device such that the distal end opening portion t of the tip 12 accesses one holding recess 3 which carries the selected cell C. Then, the piston mechanism (the suction motor 82 to be described later) of the one head device is driven to cause the tip 12 to suction the cell C. The same suction step is sequentially executed with respect to the tips 12 attached to the other heads 61.

Subsequently, a step of moving the head unit 6 to a mounting position of the microplate 4 is executed. In this step, with each tip 12 of the head group 6H suctioning the cell C, the head unit 6 is moved along the guide rail 6G from a position above the selection container 11 to a position above the microplate 4.

Thereafter, a step of causing the cell C to be discharged from the tip 12 is executed. In the discharge step, all the heads 61 (the tips 12) of the head group 6H are simultaneously lowered. In other words, all the heads 61 are moved downward (the −Z direction) by driving the raising and lowering mechanisms (the drive motor 81 to be described later) provided in all the head devices such that the distal end opening portions t of all the tips 12 enter the respective wells 41 as shown in FIG. 5. Then, the piston mechanisms (the suction motor 82 to be described later) of all head devices are driven to cause all the tips 12 to simultaneously discharge the cells C. The discharge status of these cells C is checked by capturing an image of the microplate 4 by the camera unit 5.

Figure 6:
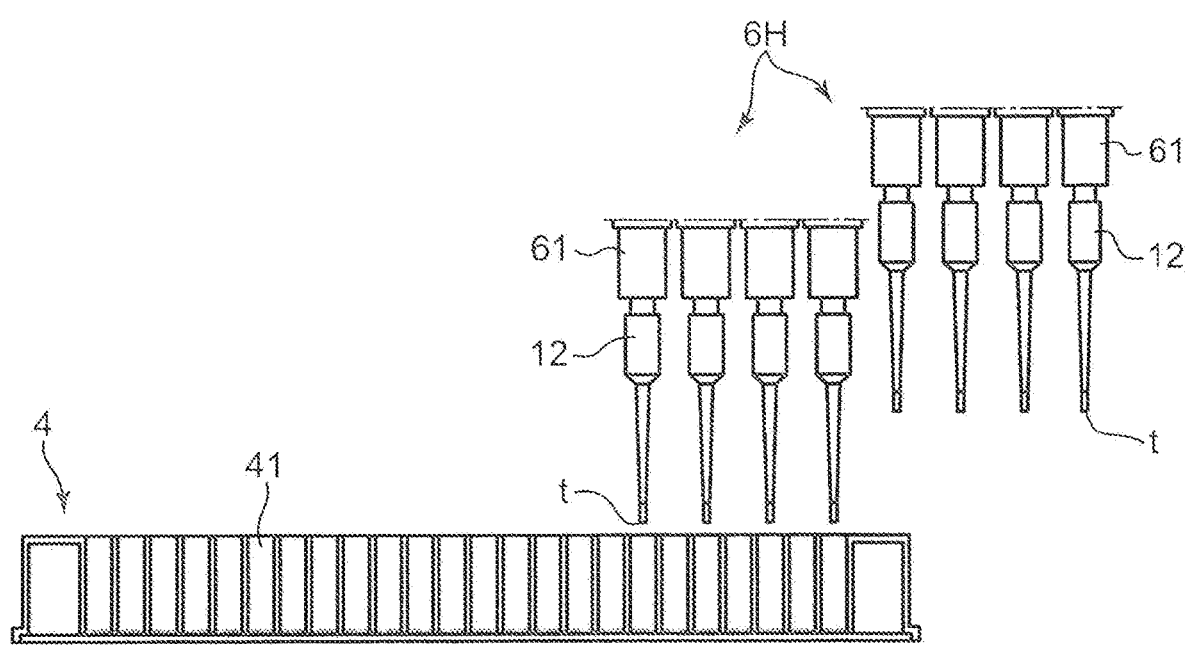
FIG. 6 is a view for explaining another example of the simultaneous discharge.

In the discharge step, simultaneous discharge of the cells C from all the tips 12 is not essential. Similarly to the suction step, discharge of the cells C may be conducted on a tip 12 basis. Alternatively, the simultaneous discharge may be conducted by a part of the group of the tips 12 that are capable of simultaneous discharge. FIG. 6 is a view for explaining another example of the simultaneous discharge. Here, a state is illustrated in which, among all the eight heads 61 (the tips 12), only four heads 61 are lowered, and the tips 12 attached to the four heads 61 access the wells 41.

The simultaneous discharge is not limited to a mode where the cells C are discharged from all the tips 12 at exactly the same timing. For example, with all the heads 61 set to be lowered simultaneously, discharge timing of the cell C may have a slight time difference for each head 61. For example, there might occur a case where the tip 12 enters the well 41 with an inappropriate positional relation. In this case, it is preferable to cause the cell C to be discharged after slightly moving the tip 12 (the head 61) during the simultaneous discharge.

Figure 7:
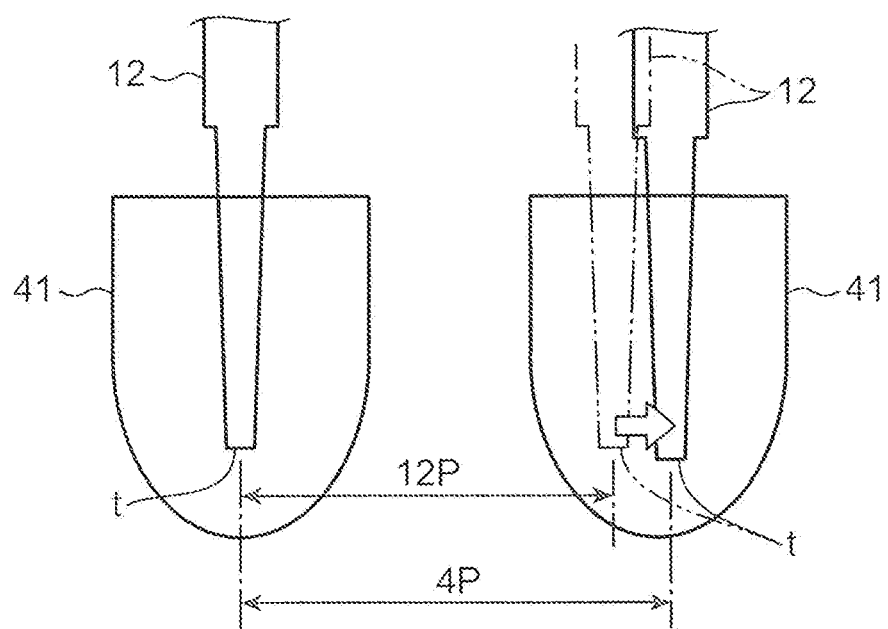
FIG. 7 is a view for explaining discharge operation executed when positional displacement occurs between the tip and the well.

FIG. 7 is a view for explaining discharge operation executed when positional displacement occurs between the tip 12 and the well 41. For example, there is a case where due to a molding error of the microplate 4 (the well 41), an installation error of the head 61, or the like, the tip 12 is not lowered to an intended position. FIG. 7 illustrates an example where the tip alignment pitch 12P is not exactly an integral multiple of the well pitch 4P. In this case, as indicated by a dotted line in the figure, the tip 12 enters a position displaced from a hole core of the well 41. When discharge of the cell C is conducted in this state, there might occur a case where the cell C is not stationarily arranged at a desired position of the well 41. Accordingly, in this case, it is preferable to cause the right tip 12 in FIG. 7 to discharge the cell C after causing the left tip 12 to discharge the cell C and then slightly moving the head unit 6 to be aligned with the well 41 corresponding to the right tip 12.

Specific Configuration of Head Unit

Figure 8:
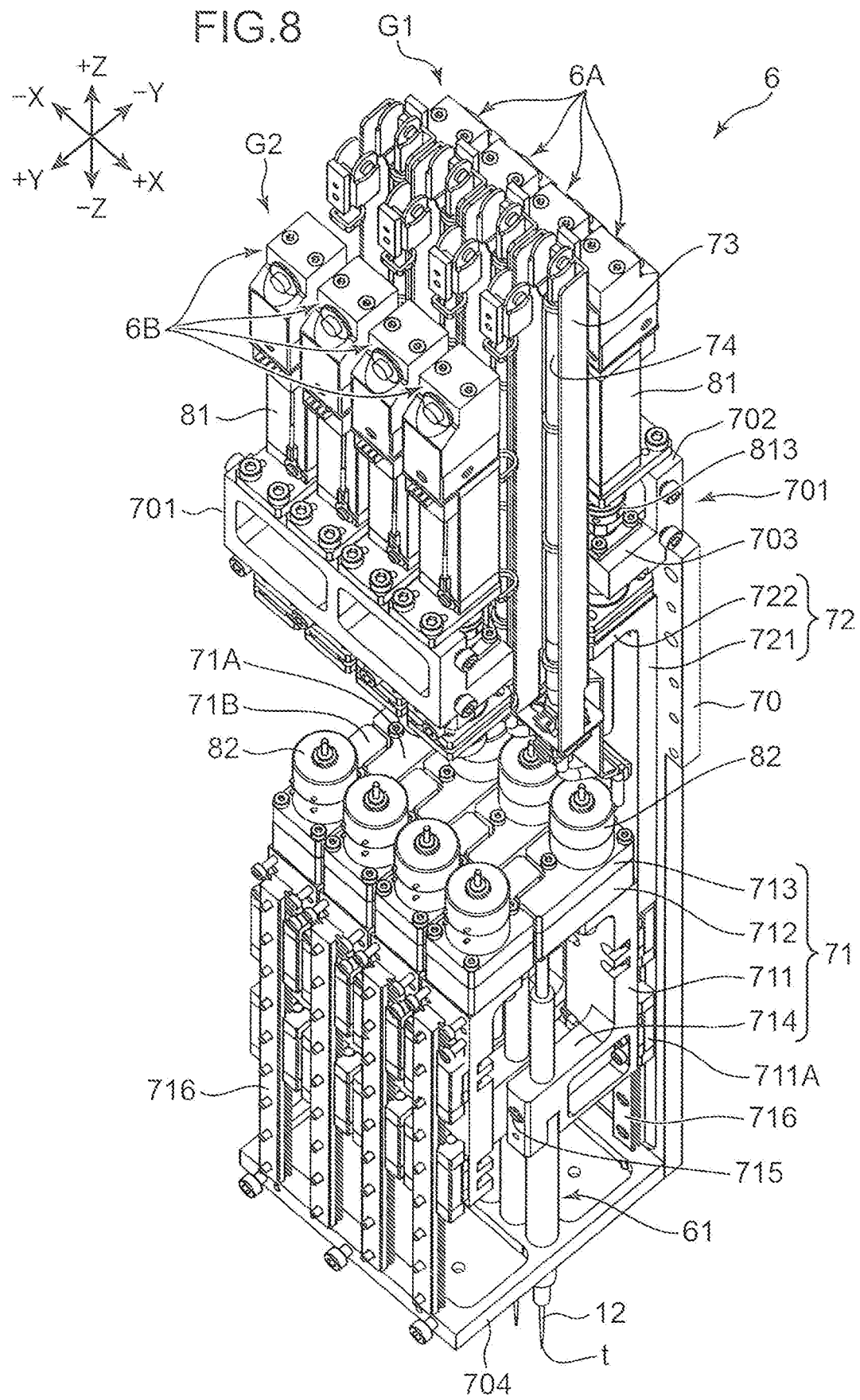
FIG. 8 is a perspective view of the head unit with a head cover removed.
Figure 9:
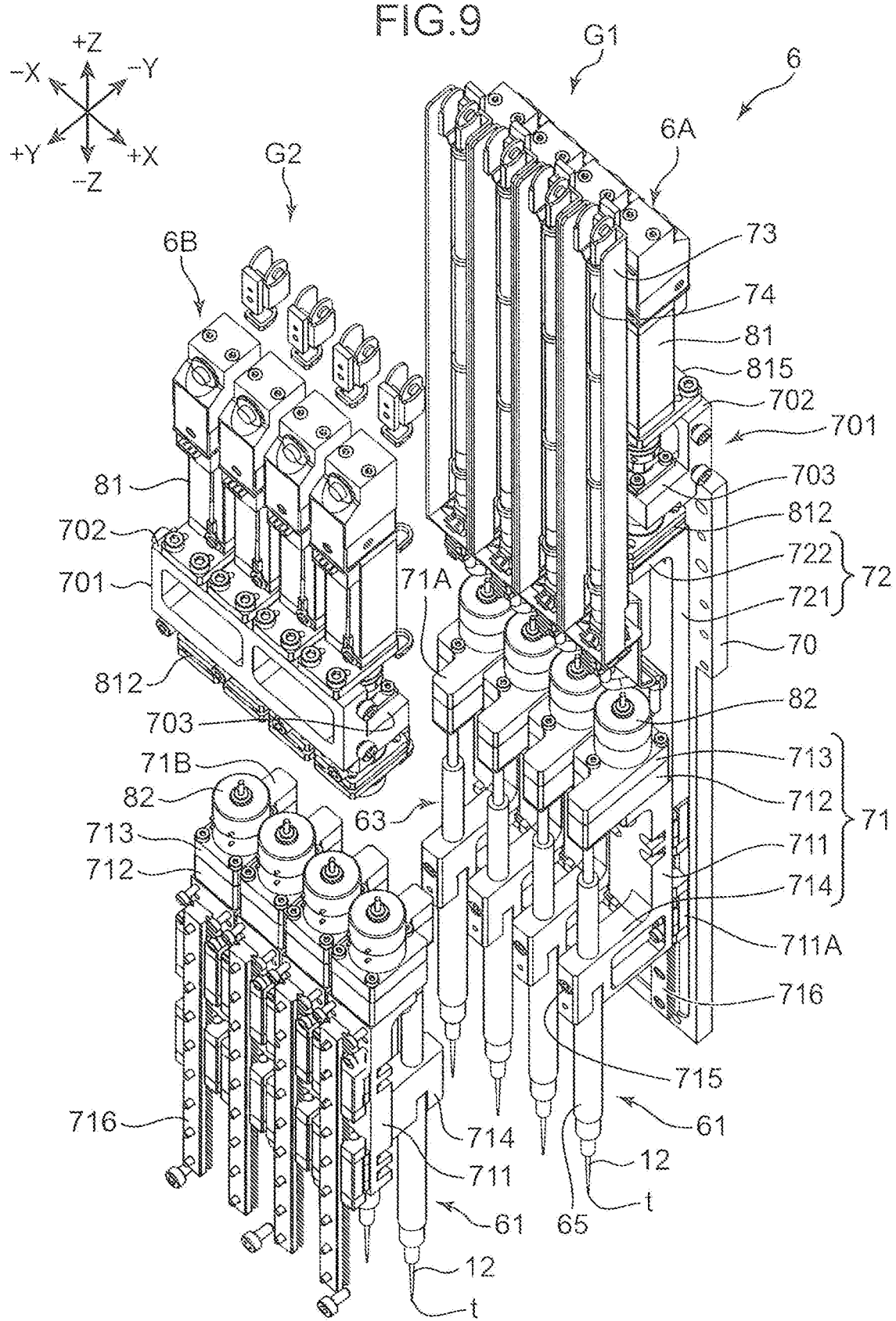
FIG. 9 is an exploded perspective view of the head unit shown in FIG. 8.
Figure 10:
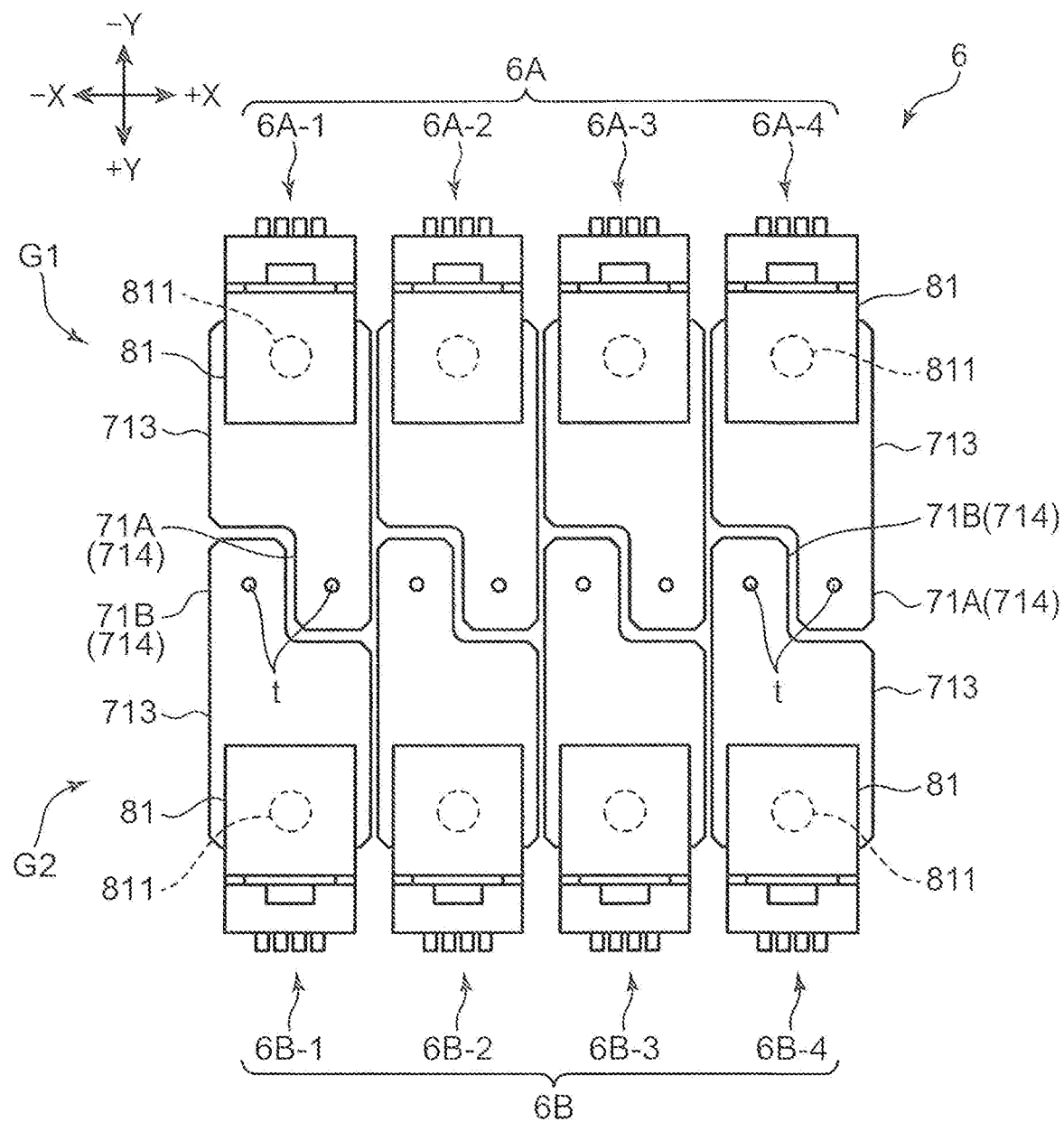
FIG. 10 is a top view of the head unit.
Figure 11:
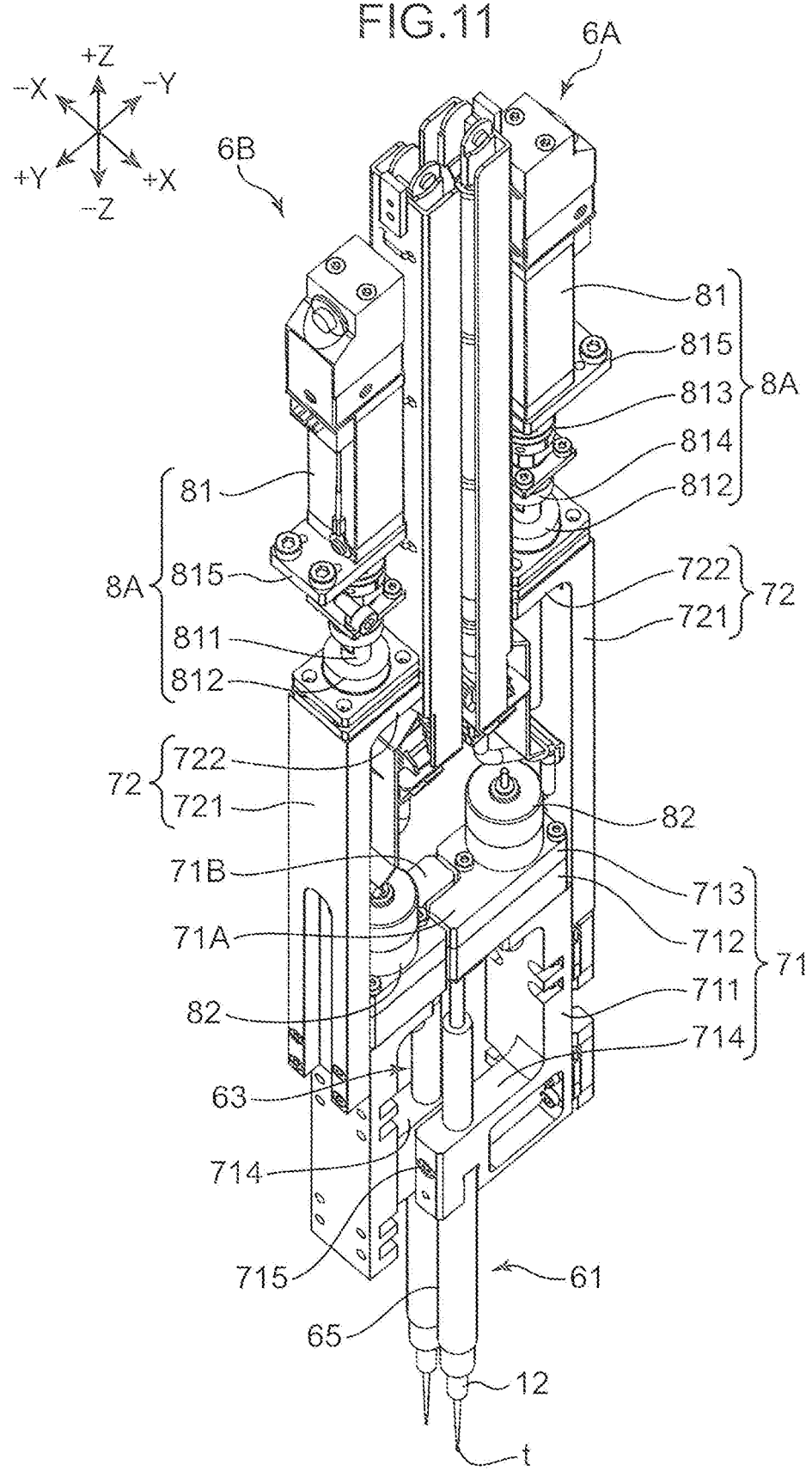
FIG. 11 is a perspective view showing a state of a pair of head devices fit to each other on a +Y side and a −Y side.
Figure 12:
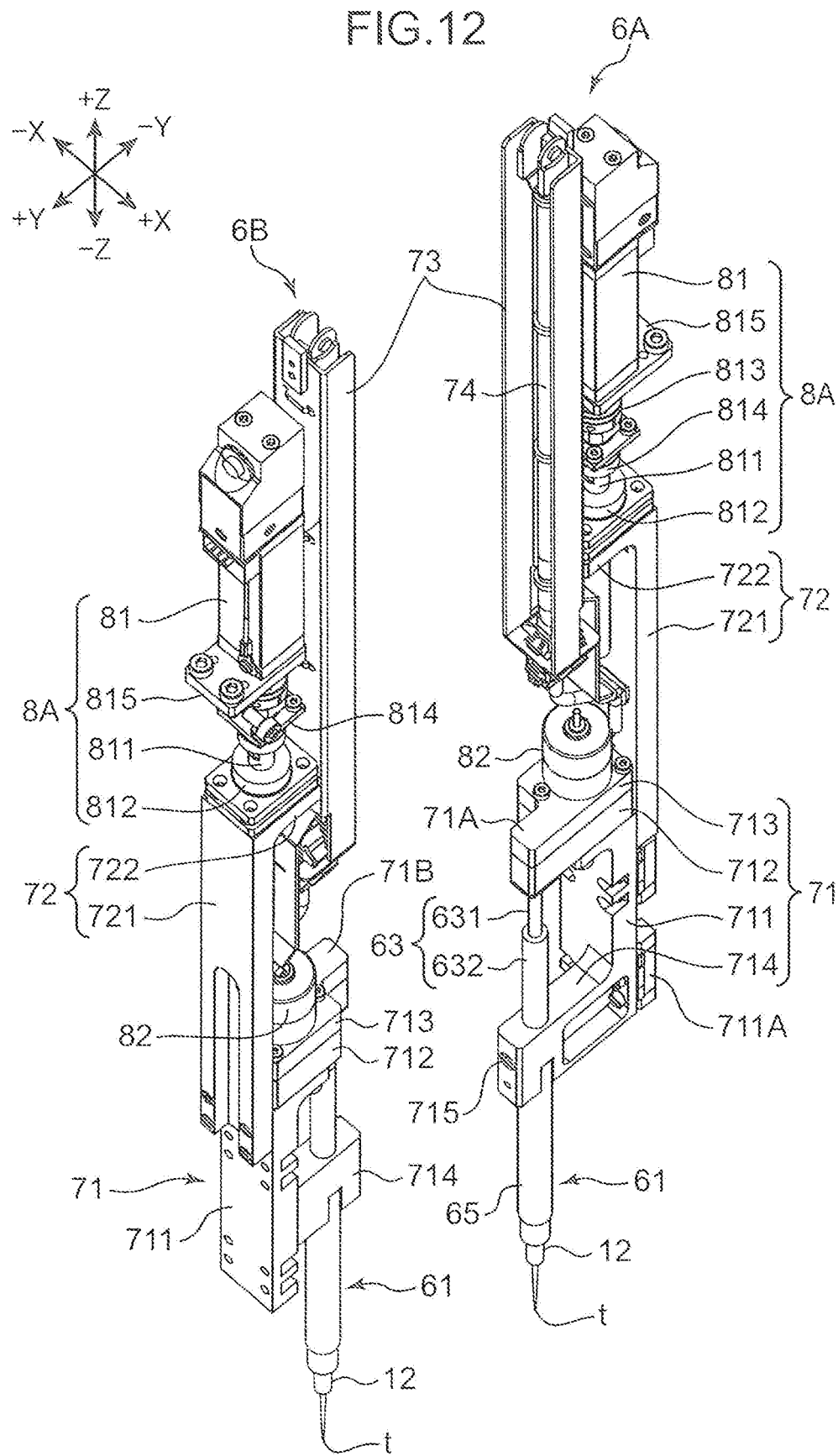
FIG. 12 is a perspective view showing a state of the pair of head devices shown in FIG. 11 and being separated on the +Y side and the −Y side.
Figure 13:
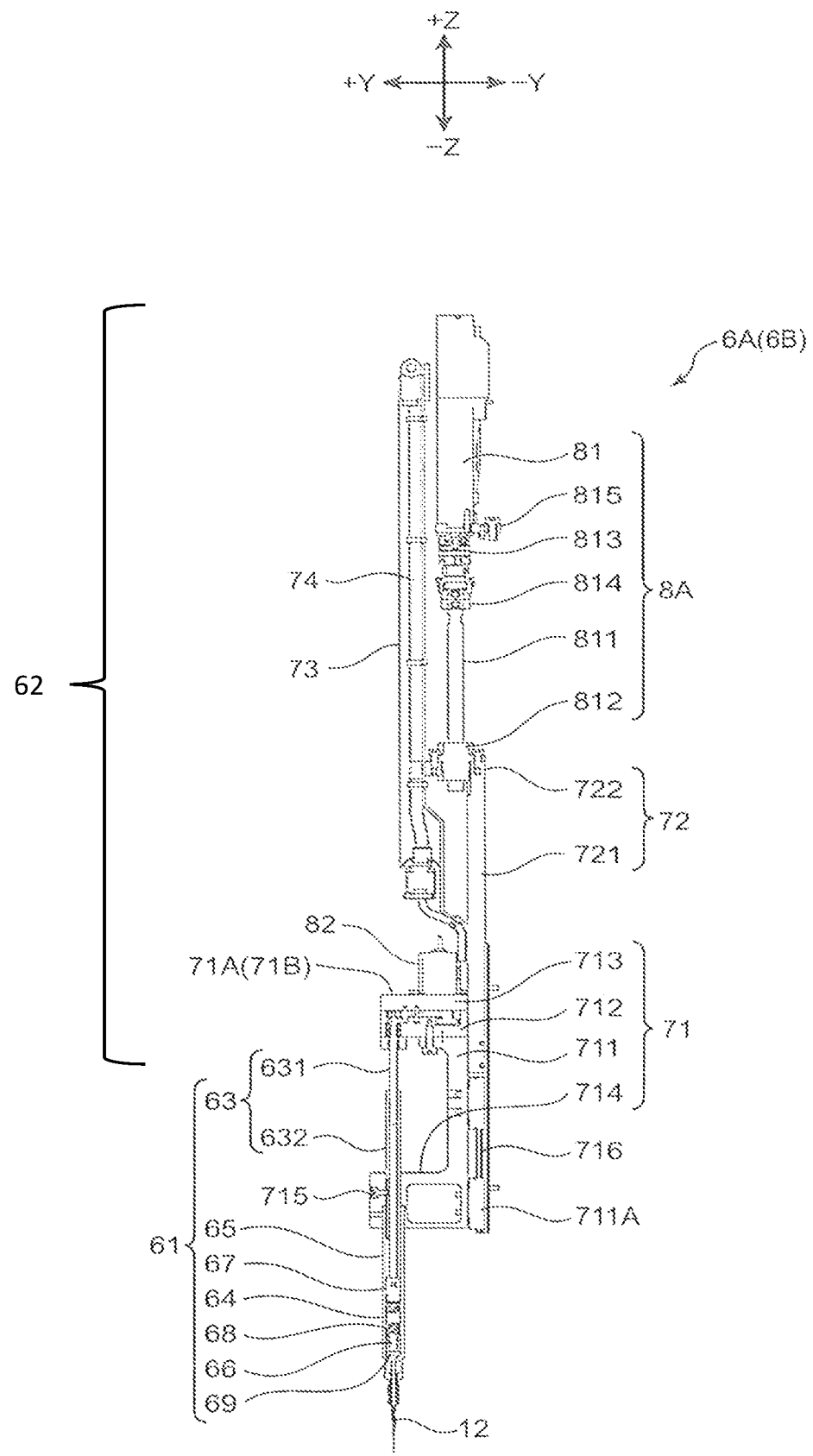
FIG. 13 is a side sectional view of the head device.
Figure 14:
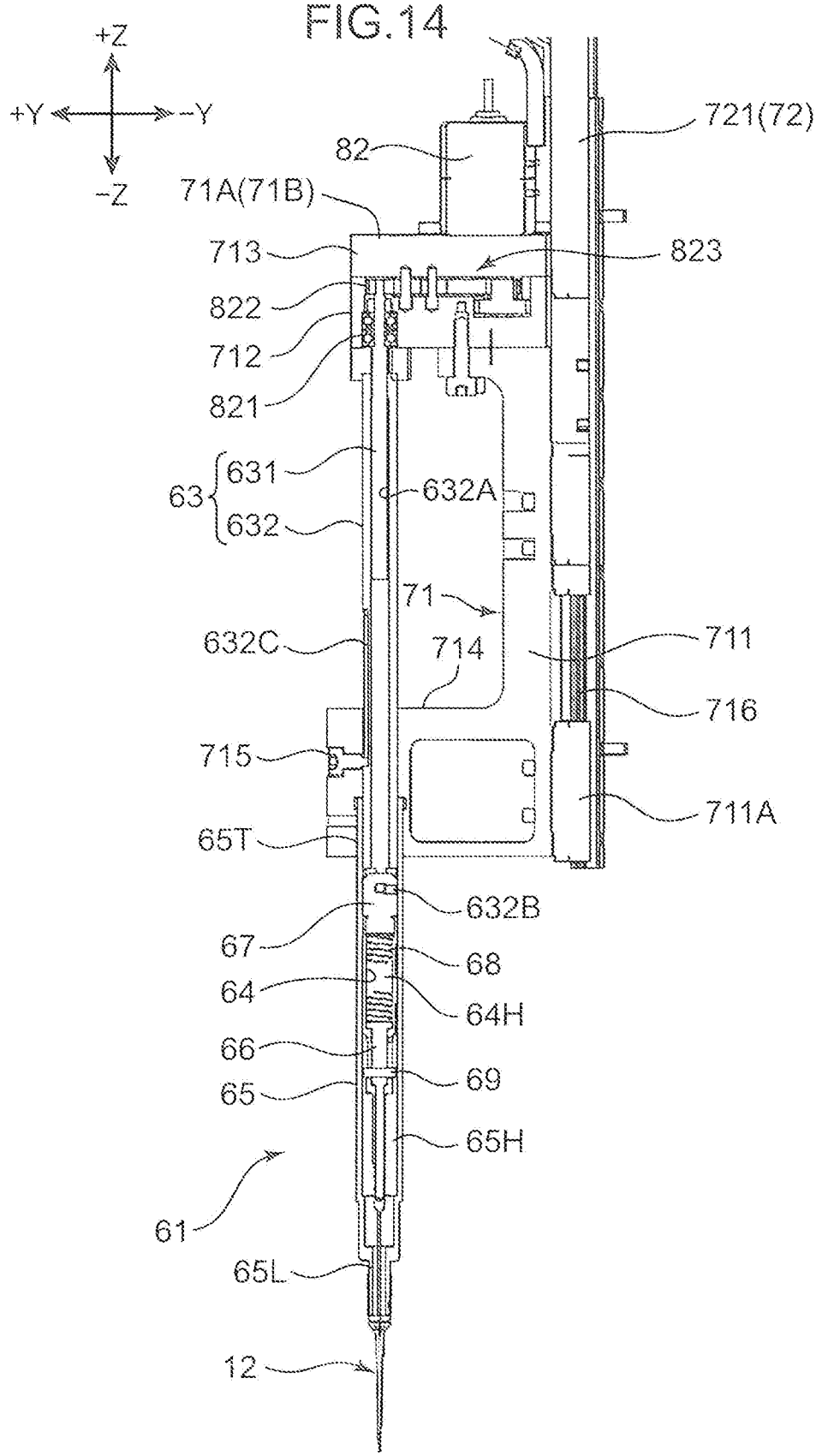
FIG. 14 is an enlarged view of a main part shown in FIG. 13.

In the following, description will be made of a specific configuration of the head unit 6 capable of realizing the above simultaneous discharge with reference to FIG. 8 to FIG. 14. FIG. 8 is a perspective view of the head unit 6 with the head cover 621 removed, FIG. 9 is an exploded perspective view of the head unit 6, and FIG. 10 is a top view of the head unit 6. FIG. 11 is a perspective view showing a state of a pair of head devices 6A and 6B fit to each other on a +Y side and a −Y side, and FIG. 12 is a perspective view showing a state of the pair of the head devices 6A and 6B being separated on the +Y side and the −Y side. FIG. 13 is a side sectional view of one head device 6A, and FIG. 14 is an enlarged view of a main part shown in FIG. 13.

Overall Configuration of Head Unit

The head unit 6 is configured by an assembly including a head device group G1 (a first group) on the −Y side and a head device group G2 (a second group) on the +Y side. The head device group G1 includes four head devices 6A arranged in the X direction and the head device group G2 also includes four head devices 6B arranged in the X direction, the head device group G1 and the head device group G2 being assembled to be opposed to each other in the Y direction. The head devices 6A and 6B each include the head 61 on the −Z side.

As shown in FIG. 8 and FIG. 9, the head device group G1 on the −Y side is fit in a unit frame 70 arranged on the −Y side and extending in the Z direction. An upper end frame 701 is attached to a +Z side end portion of the unit frame 70. The upper end frame 701 includes an upper supporting portion 702 having an L-shape viewed in the X direction and positioned on an extension line on the +Z side of the unit frame 70, and a lower supporting portion 703 extending in the +Y direction from the unit frame 70. Guide rails 716 extending in the Z direction are attached to the unit frame 70 so as to each correspond to each of the four head devices 6A. The guide rail 716 extends from the vicinity of the center of the unit frame 70 in the Z direction to the vicinity of the −Z side end portion.

Although not illustrated, the head device group G2 on the +Y side is also fit in a unit frame similar to the above which is arranged on the +Y side and extends in the Z direction. In FIG. 8 and FIG. 9, the upper end frame 701 and the four guide rails 716 which are attached to the unit frame on the −Y side. A −Z end portion of the unit frame 70 on the −Y side and a −Z end portion of the unit frame on the +Y side (not shown) are bridged by a lower end frame 704 (illustrated only in FIG. 8). In the center of the lower end frame 704 in the Y direction, eight through-holes are bored to allow the eight heads 61 to pass through in the Z direction, respectively.

Configuration of Each Head Device

The eight head devices 6A and 6B have the same configuration. With reference to FIG. 12 to FIG. 14, a configuration of one head device 6A will be described. Each head device 6A includes the head 61 to which the tip 12 is attached, a first frame portion 71 (frame member) which holds the head 61, a second frame portion 72 (frame member) to which the first frame portion 71 is attached and which moves in the Z direction, a raising and lowering mechanism 8A which causes the second frame portion 72 to move in the Z direction, and the suction motor 82 which is mounted on the first frame portion 71 and generates driving force for causing the tip 12 to suction and discharge the cell C.

The raising and lowering mechanism 8A includes the drive motor 81, a ball thread shaft 811, a nut member 812, a coupling 813, an upper end bearing 814, and a motor supporting plate 815. The drive motor 81 is a motor which is mounted on the head unit 6 so as to correspond to each head 61 and generates driving force for causing the head 61 to move along the Z direction. In the present embodiment, the drive motor 81 generates rotation driving force which causes forward rotation or reverse rotation of the ball thread shaft 811 around an axis.

The ball thread shaft 811 extends in the Z direction and has a circumferential surface threaded with a male screw. The nut member 812 has a female screw on its inner surface and is screwed on the ball thread shaft 811. Forward rotation or reverse rotation of the ball thread shaft 811 by the drive motor 81 causes the nut member 812 to move in the +Z or the −Z direction. The coupling 813 is a member which connects an output shaft of the drive motor 81 and an upper end of the ball thread shaft 811. The upper end bearing 814 rotatably supports the upper end of the ball thread shaft 811. The upper end bearing 814 includes a tubular portion and a flange portion, the tubular portion being fit in a through-hole provided in the lower supporting portion 703 of the upper end frame 701 and the flange portion being held on an upper surface of the lower supporting portion 703. The motor supporting plate 815 is a flat plate which supports the drive motor 81. The motor supporting plate 815 is screwed on the upper supporting portion 702 of the upper end frame 701 to support a lower surface side of the drive motor 81.

The first frame portion 71 includes a vertical frame 711 extending in the Z direction, a holding frame 712 fit into a +Z end portion of the vertical frame 711 and protruding in the +Y direction, a motor supporting frame 713 fit on the holding frame 712, and a head holding frame 714 protruding in the +Y direction from a −Z end portion side of the vertical frame 711. A guide portion 711A to be engaged with the guide rail 716 of the unit frame 70 is attached to a side surface on the −Y side of the vertical frame 711.

The suction motor 82 is supported by the motor supporting frame 713. The motor supporting frame 713 has a base portion having an X direction width larger than a size of the suction motor 82 and supporting the suction motor 82, and a narrow width portion 71A (a narrow width portion 71B in the head device 6B) protruding in the +Y direction from the base portion and having an X direction width about half that of the base portion. The head holding frame 714 is provided to protrude at a position overlapping the narrow width portion 71A in the up-down direction, and has approximately the same X direction width as that of the narrow width portion 71A.

The second frame portion 72, which is an L-shaped frame connected to the raising and lowering mechanism 8A and to be moved in the Z direction by the raising and lowering mechanism 8A, includes a vertical portion 721 extending in the Z direction and a horizontal portion 722 protruding in the +Y direction from a +Z end portion of the vertical portion 721. The first frame portion 71 is fixed to a vicinity of a −Z end portion of the vertical portion 721. The horizontal portion 722 includes a through-hole formed in the Z direction, and the nut member 812 of the raising and lowering mechanism 8A is fixed to the horizontal portion 722 while being fit in the through-hole. Accordingly, when the ball thread shaft 811 is driven to rotate by the drive motor 81, thereby causing the nut member 812 to move in the −Z or +Z direction, the second frame portion 72 and the first frame portion 71 connected thereto are also moved in the −Z or +Z direction in association with the movement of the nut member. At the time of this movement, the guide portion 711A of the first frame portion 71 is guided by the guide rail 716. A cable tray 73 is attached to a +Y side end surface of the horizontal portion 722. The cable tray 73 holds a feeding cable 74 of the suction motor 82.

Details of Head

A configuration of the head 61 will be described in detail with reference to FIG. 13 and FIG. 14. The head 61 includes a shaft member 63, a first tubular rod 64, a second tubular rod 65, a discharge rod 66, a connection piece 67, a coil spring 68, and a stopper 69 arranged in the Z direction.

The shaft member 63, which is a screw shaft with an outer circumferential surface threaded with a male screw, includes a first screw shaft 631 to which rotation driving force is applied, and a tubular second screw shaft 632 screwed with the first screw shaft 631. The second screw shaft 632 includes an a upper end portion 632A threaded with a female screw which engages with the male screw of the first screw shaft 631, and a lower end portion 632B to which the first tubular rod 64 is attached via the connection piece 67. Forward rotation or reverse rotation of the first screw shaft 631 around an axis causes the second screw shaft 632 to move in the −Z or +Z direction. An upper end portion of the first screw shaft 631 is rotatably supported by a bearing 821. An input gear 822 is attached to an uppermost end of the first screw shaft 631.

The suction motor 82 generates rotation driving force which causes forward rotation or reverse rotation of the first screw shaft 631 around an axis. A gear unit 823 is interposed between an output shaft of the suction motor 82 and the input gear 822. Rotation driving force of the suction motor 82 is transmitted to the input gear 822 through the gear unit 823 to cause the first screw shaft 631 to rotate. The bearing 821 and the gear unit 823 are held by the holding frame 712.

On a circumferential wall of the second screw shaft 632 in the vicinity of a middle portion in the Z direction, a long hole 632C which extends in the Z direction is provided. A distal end portion of a guide pin 715 is fit into the long hole 632C. The guide pin 715 includes a portion screwed on the head holding frame 714, and the distal end portion provided continuous with the screwed portion. As described above, when the first screw shaft 631 rotates around the axis, the second screw shaft 632 moves in the Z direction. At this time, the second screw shaft 632 does not rotate around an axis but has movement in the Z direction guided by the guide pin 715 fit in the long hole 632C. The long hole 632C has a length in the Z direction which corresponds to a movement range of the second screw shaft 632.

The first tubular rod 64 is a cylindrical member internally provided with a tubular space 64H which houses the discharge rod 66 and the coil spring 68. An inner wall partitioning the tubular space 64H is engraved with a screw groove. Screwing the screw groove with a screw portion provided in the connection piece 67 brings the first tubular rod 64 into connection with the second screw shaft 632 (the shaft member 63). As a result, the first tubular rod 64 is allowed to move integrally with the second screw shaft 632 in the Z direction.

The discharge rod 66 is a member for causing the plunger 14 (FIG. 4) of the tip 12 to move in the Z direction. The discharge rod 66 is housed in the tubular space 64H of the first tubular rod 64 so as to be movable in the Z direction with respect to the first tubular rod 64. A −Z end portion of the discharge rod 66 is attached to the hollow portion 14H of the plunger base end portion 141. The stopper 69 is a pin member which causes the first tubular rod 64 and the discharge rod 66 to be engaged with each other. The stopper 69 is inserted through a long hole bored in the first tubular rod 64 and a stopper hole bored in the discharge rod 66 to regulate a Z direction movement range of the discharge rod 66 in the tubular space 64H.

The coil spring 68 is interposed between the connection piece 67 and the discharge rod 66 in the tubular space 64H. Since the connection piece 67 is screwed on the first tubular rod 64, the coil spring 68 generates pressing force which presses the discharge rod 66 downward. The pressing force causes a part of the discharge rod 66 to abut against a part of the first tubular rod 64. Abutment caused by the pressing force causes the discharge rod 66 to move in association with up and down movement of the shaft member 63. Interference of the stopper 69 with an engagement portion of the second tubular rod 65 prevents the above associative movement of the discharge rod 66 to compress the coil spring 68.

The second tubular rod 65 is a cylindrical body having an outer diameter increased in three steps from −Z toward +Z and includes a housing space 65H which houses the first tubular rod 64 so as to be movable in the Z direction. A hollow portion 13H (FIG. 4) provided in the syringe base end portion 131 of the syringe 13 is attached to a lower end 65L of the second tubular rod 65.

An upper end portion 65T of the second tubular rod 65 is fixedly held by the head holding frame 714. Accordingly, the second tubular rod 65 moves integrally with the first frame portion 71 in the Z direction but does not move relative to the first frame portion 71. In other words, since the first tubular rod 64 moves in association with the second screw shaft 632, the first tubular rod moves relative to the first frame portion 71 but the second tubular rod 65 is immovable.

Thus configured head 61 and the driving force of the suction motor 82 enable the tip 12 to operate to suction and discharge the cell C. Specifically, associative movement of the discharge rod 66 with the movement of the second screw shaft 632 in the Z direction causes the plunger 14 attached to the discharge rod 66 to reciprocate in the tubular passage of the syringe 13, thereby realizing suction of the cell C from the distal end opening portion t into the tip 12 and discharge of the suctioned cell C from the distal end opening portion t.

During suction operation of the cell C, the first screw shaft 631 is driven to rotate by the suction motor 82 such that the second screw shaft 632 moves upward (+Z). When the second screw shaft 632 is raised, the first tubular rod 64 connected to the second screw shaft 632 is also integrally raised. The discharge rod 66 brought into a state of engagement with the first tubular rod 64 by pressing force of the coil spring 68 also moves in association with the movement of the first tubular rod. Therefore, the plunger 14 attached to the discharge rod 66 moves upward of the syringe 13 attached to the immovable second tubular rod 65. This enables suction of the cell C into the tubular passage of the syringe 13.

During discharge operation of the cell C, the first screw shaft 631 is driven to rotate by the suction motor 82 such that the second screw shaft 632 moves downward (−Z). When the second screw shaft 632 is lowered, the first tubular rod 64 connected to the second screw shaft 632 is also integrally lowered. Additionally, the discharge rod 66, which is engaged with the first tubular rod 64 by the pressing force of the coil spring 68, also moves in association with the lowering of the second screw shaft 632. Therefore, the plunger 14 attached to the discharge rod 66 is moved downward so as to be inserted into the syringe 13. As a result, the cell C suctioned once into the tip 12 is discharged from the distal end opening portion t.

Layout of Head Device

With reference to FIG. 8 to FIG. 12, mainly to FIG. 10, description will be made of layout of the eight head devices 6A and 6B in the head unit 6. The head 61 of each of the eight head devices 6A and 6B, i.e., each head 61 of the head group 6H provided in the head unit 6 is linearly aligned in the X direction (the second direction). By contrast, the drive motors 81 and the suction motors 82 provided in the head unit 6 are separately arranged on the −Y side (one side in the third direction) and on the +Y side (the other side in the third direction) in the Z direction (the first direction) with the head group 6H provided therebetween in a plan view.

To be specifically described, the head unit 6 includes the four head devices 6A of the head device group G1 on the −Y side and the four head devices 6B of the head device group G2 on the +Y side. The drive motor 81 and the suction motor 82 mounted on each of the head devices 6A on the −Y side are arranged on the −Y side relative to an alignment line of the head group 6H. By contrast, the drive motor 81 and the suction motor 82 mounted on each of the head devices 6B on the +Y side are arranged on the +Y side relative to the alignment line of the head group 6H.

Specifically, the eight heads 61 (a plurality of heads) of the head group 6H are divided into the four heads 61 (referred to as first heads 61 herein) belonging to the head device group G1 (the first group) on the −Y side and the four heads 61 (referred to as second heads 61 herein) belonging to the head device group G2 (the second group) on the +Y side. The second head 61 is arranged adjacent to the first head 61 in the X direction. In other words, the plurality of heads in the head group 6H are aligned such that the first head 61 and the second head 61 are aligned alternately in the X direction.

Then, the first head 61 is each driven by the drive motor 81 arranged on the −Y side (raised or lowered through the first frame portion 71 and the second frame portion 72) and the second head 61 is each driven by the drive motor 81 arranged on the +Y side. The suction motor 82 arranged on the −Y side is applied to each tip 12 attached to the first head 61 and the suction motor 82 arranged on the +Y side is applied to each tip 12 attached to the second head 61.

The reason why the drive motor 81 and the suction motor 82 are arranged in such layout is that the drive motor 81 and the suction motor 82 have sizes too large for the required tip alignment pitch 12P (FIG. 4 and FIG. 5). As described above, for realizing simultaneous discharge from the plurality of tips 12 under the well pitch 4P of the microplate 4, it is necessary, for example, to set the tip alignment pitch 12P to 9.0 mm. However, a size of the motor capable of generating required driving force for raising and lowering operation of the head 61 and suction operation of the tip 12 will be larger than the tip alignment pitch 12P. In other words, the drive motor 81 and the suction motor 82 cannot be aligned according to the required tip alignment pitch 12P. Therefore, the drive motor 81 and the suction motor 82 are arranged separately on the −Y side and the +Y side to prevent adjacent drive motors 81 and adjacent suction motors 82 from interfering with each other while aligning the tips 12 at a required tip alignment pitch 12P.

Description will be made of improvement in a shape of the head devices 6A and 6B for realizing the above layout. With reference to FIG. 11 and FIG. 12, a pair of head device 6A on the −Y side and the head device 6B on the +Y side arranged at the same position in the X direction are installed in the head unit 6 so as to be opposed to each other in the Y direction.

The second frame portion 72 connected to the raising and lowering mechanism 8A and the motor supporting plate 815 which supports the drive motor 81 have a predetermined width (a first width) in the X direction. As the predetermined width, a X direction width equal to or larger than the X direction width (e.g. 9 mm) of the drive motor 81 is required in order to stably hold each of the nut members 812 and the drive motors 81. Also for the first frame portion 71, a base portion supporting the suction motor 82 needs an X direction width equal to or larger than the X direction width (e.g. 9 mm) of the suction motor 82.

By contrast, the head holding frame 714 of the first frame portion 71 which holds the head 61 needs only an X direction width (a second width) about half that of the base portion as already described because the head 61 (the second tubular rod 65) has an outer diameter smaller than those of the drive motor 81 and the suction motor 82. Portions of the holding frame 712 and the motor supporting frame 713, the portions holding an upper end of the head 61, also need only an X direction width about half that of the base portion, and therefore, the above-described narrow width portions 71A and 71B are formed.

In the head device 6A on the −Y side, the narrow width portion 71A protrudes from a +X side portion of the base portion of the motor supporting frame 713 toward the +Y direction. The head holding frame 714 also protrudes, in the +Y direction, at a +X side portion of a lower end of the vertical frame 711. The first and second frame portions 71 and 72 of the head device 6B on the +Y side have the same shape as those of the head device 6A on the −Y side and are obtained by turning those of the head device 6A by 180°. The narrow width portion 71B of the head device 6B protrudes, in the −Y direction, at a −X side portion of the base portion of the motor supporting frame 713, and the head holding frame 714 protrudes, in the −Y direction, at a −X side portion of the lower end of the vertical frame 711.

When the pair of head devices 6A and 6B are combined in the Y direction, the narrow width portion 71B fits into a side space on the −X side of the narrow width portion 71A to make the narrow width portions 71A and 71B be adjacent to each other in the X direction. Similarly, the head holding frames 714 of the head devices 6A and 6B are also brought to be adjacent to each other in the X direction. As a result, the heads 61 of the head devices 6A and 6B are also brought to be adjacent to each other in the X direction.

As shown in FIG. 8 to FIG. 10, in the present embodiment, four pairs of head devices 6A and 6B shown in FIG. 11 and FIG. 12 are installed in the head unit 6 so as to be adjacent to each other in the X direction. Description will be further made with reference to FIG. 10, the head device group G1 on the −Y side includes four head devices 6A-1, 6A-2, 6A-3, and 6A-4 aligned in the X direction and the head device group G2 on the +Y side includes four head devices 6B-1, 6B-2, 6B-3, and 6B-4 aligned in the X direction.

In a portion where both the head device groups G1 are G2 are opposed to each other, four each of the narrow width portions 71A and 71B protrude in a comb tooth manner to be meshed with each other. As a result of the meshing, the narrow width portions 71A and 71B are alternately aligned in the X direction to realize linear alignment of the heads 61 in the X direction (the distal end opening portion t of the tip 12). Additionally, the drive motors 81 (the suction motors 82) of the head devices 6A-1 to 6A-4 and the drive motors 81 (the suction motors 82) of the head devices 6B-1 to 6B-4 are linearly aligned on the −Y side and the +Y side in the X direction. As a result, the eight heads 61 (the tips 12) are aligned in the X direction at an alignment pitch half an alignment pitch of the drive motor 81 (the suction motor 82). Thus, separately arranging the drive motors 81 and the suction motors 82 provided in the head devices 6A and 6B, respectively, on the −Y side and the +Y side ensures an arrangement space and also enables the heads 61 to be arranged at a pitch which makes the heads as close to each other as possible in the X direction.

Operations and Effects

According to the cell transfer device S according to the above-described present embodiment, the plurality of drive motors 81 are separately arranged on the −Y side and the +Y side with the head group 6H provided therebetween. Even when the drive motor 81 has a large size compared to the head 61 (the tip 12), an alignment pitch in the X direction of the tip 12 can be set short without making these motors interfere with each other. For example, as shown in FIG. 5, the tips 12 can be aligned at the tip alignment pitch 12P that is twice the well pitch 4P. Even when a discharge destination of the cell C is limited to a narrow area, this enables simultaneous discharge of the cells C from the plurality of tips 12.

Each of the head devices 6A and 6B includes the suction motor 82 which generates driving force for causing each tip 12 to suction and discharge the cell C. This realizes suction and discharge of the cell C on a tip 12 basis. The suction motors 82 are also separately arranged on the −Y side and the +Y side with the head group 6H provided therebetween. Accordingly, even when the suction motor 82 has a large size compared to the head 61 (the tip 12), an alignment pitch of the tip 12 in the X direction can be set short.

The four first heads 61 belonging to the head device group G1 on the −Y side and the four second heads 61 belonging to the head device group G2 on the +Y side are alternately aligned linearly in the X direction. The tips 12 attached to these first and second heads enable simultaneous suction of the cells C linearly aligned at a predetermined pitch and simultaneous discharge of the cells C to discharge positions linearly aligned at a predetermined pitch. Then, since the drive motor 81 and the suction motor 82 of each head 61 of the head device groups G1 and G2 are arranged separately on the −Y side and the +Y side with the head group 6H provided therebetween, a linear alignment pitch of the tip 12 in the X direction can be set short.

Additionally, according to the cell transfer method using a cell transfer device S, the cell transfer device S is used which includes the tips 12 aligned at a tip alignment pitch 12P that is n-times the well pitch 4P. This arrangement allows the distal end opening portions t of the plurality of tips 12 to simultaneously enter the wells 41 of the microplate 4. Accordingly, simultaneous discharge of the cells C from the plurality of tips 12 can be realized to efficiently process the cell transfer work. Further, since the cell C can be suctioned from the dish 2 by the tip 12 on a head 61 basis, the dish 2 can be used which does not depend on the alignment pitch of the tip 12. Accordingly, the dish 2 with a compact size can be used.

Description of Modified Embodiment

Although the embodiments of the present disclosure have been described in the foregoing, the present disclosure is not limited thereto and can further assume various modified embodiments. For example, although the above embodiment illustrates an example where the narrow width portions 71A and 71B and the heads 61 (the distal end opening portions t of the tips 12) of the head device groups G1 and G2 on the −Y side and the +Y side are alternately aligned in the X direction, a part of these components may not necessarily be alternately aligned.

Figure 15:
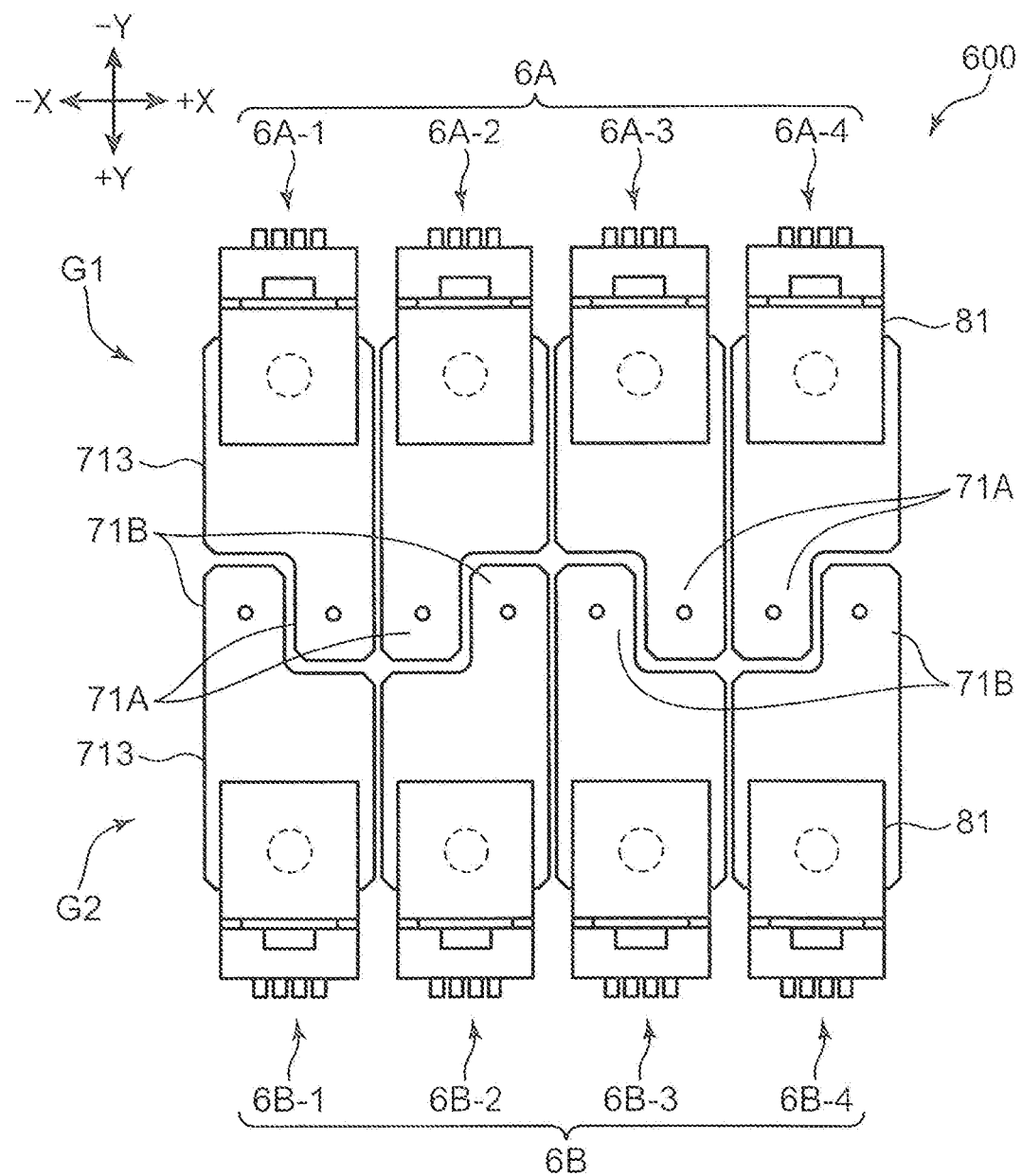
FIG. 15 is a top view of a head unit according to a modification.

FIG. 15 is a top view of a head unit 600 according to a modification. Here, protrusion positions of the narrow width portions 71A (the heads 61) of the head devices 6A -2 and 6A-4 are on the −X side of the motor supporting frame 713, opposite to the example shown in FIG. 10. In accordance with this arrangement, protrusion positions of the narrow width portions 71B (the heads 61) of the head devices 6B-2 and 6B-4 are on the +X side of the motor supporting frame 713.

As a result, the head devices 6A-1, 6A-2 and the head device 6A-3, 6A-4 belonging to the same group are adjacent to each other in the X direction. Similarly, the head devices 6B-2 and 6B-3 belonging to the same group are adjacent to each other in the X direction. Also in this layout, by disposing the respective drive motors 81 and the suction motors 82 on the −Y side and the +Y side, respectively, an arrangement space can be ensured and the heads 61 can be arranged at a pitch which makes the heads as close to each other as possible in the X direction. However, since there occurs a need to prepare frame members having the narrow width portions 71A and 71B with different protrusion positions, the above embodiment shown in FIG. 10 is preferable in terms of uniformalization of parts.

The above-described specific embodiments mainly include the disclosure having the following configuration.

The cell transfer device according to one aspect of the present disclosure includes a head group including a plurality of heads to which tips for suctioning and discharging cells are attached and which are capable of moving along a first direction; a head unit in which the head group is installed and which is capable of moving in a second direction orthogonal to the first direction and in a third direction orthogonal to both the first direction and the second direction; and a plurality of drive motors which are mounted on the head unit so as to each correspond to each of the heads and which generate driving force to cause the head to move along the first direction, in which the plurality of drive motors are separately arranged on one side and the other side in the third direction with the head group provided therebetween in a plan view from the first direction, and the head group includes at least a first head and a second head adjacent to the first head in the second direction, the first head being driven by the drive motor arranged on one side in the third direction, and the second head being driven by the drive motor arranged on the other side in the third direction.

According to the cell transfer device, the respective drive motors of the first head and the second head arranged adjacent to each other in the second direction are separately arranged on one side and the other side in the third direction with the head group provided therebetween. Therefore, even when the drive motor has a large size compared to the first and second heads (the tips), an alignment pitch in the second direction of the tips attached to the first and second heads can be set short without making the drive motors interfere with each other. Thus, even when a discharge destination of the cell is limited to a narrow area, the cells can be simultaneously discharged from the plurality of tips.

The above cell transfer device preferably includes a plurality of suction motors which are mounted on the head unit so as to each correspond to each of the heads, and which generate driving force to cause the tips attached to the heads to suction and discharge the cells, in which the suction motor arranged on the one side in the third direction is applied to the tip attached to the first head, and the suction motor arranged on the other side in the third direction is applied to the tip attached to the second head.

According to the cell transfer device, since the suction motor as a drive source for suction and discharge of the cell is mounted on each head, suction and discharge of the cell can be conducted on a tip basis. Then, since the suction motors are also separately arranged on the one side and the other side in the third direction with the head group provided therebetween, an alignment pitch of the tips in the second direction can be set short.

In the above cell transfer device, it is preferable that the plurality of heads provided in the head group are linearly aligned in the second direction and divided into heads belonging to a first group and heads belonging to a second group, the heads of the first group including the first head and being driven by each of the drive motors arranged on the one side in the third direction, and the heads of the second group including the second head and being driven by each of the drive motors arranged on the other side in the third direction.

According to the cell transfer device, the tips attached to the heads of the first and second groups aligned linearly enable simultaneous suction of the cells linearly aligned at a predetermined pitch and simultaneous discharge of the cells to discharge positions linearly aligned at a predetermined pitch. Then, since the drive motors of the heads of the first and second groups are separately arranged on the one side and the other side in the third direction with the head group provided therebetween, a linear alignment pitch of the tips in the second direction can be set short.

In the above cell transfer device, it is preferable that in a case where the suction motor is mounted on each head, the suction motors applied to the tips attached to the respective heads of the first group are arranged on the one side in the third direction, and the suction motors applied to the tips attached to the respective heads of the second group are arranged on the other side in the third direction.

According to the cell transfer device, since the suction motors of the respective heads of the first and second groups are also separately arranged on the one side and the other side in the third direction with the head group provided therebetween, an alignment pitch of the tips in the second direction can be set short.

In the above cell transfer device, it is preferable that the plurality of heads are aligned in which the heads belonging to the first group and the heads belonging to the second group are arranged alternately, and in a plan view from the first direction, the drive motors arranged on the one side and the other side in the third direction are linearly aligned in the second direction on the one side and the other side, respectively.

According to the cell transfer device, the heads of the first and second groups are alternately aligned in the second direction, and the drive motors of the first and second groups are also linearly aligned in the second direction on the one side and the other side in the third direction. Accordingly, compact arrangement of the heads and the drive motors can be realized and the tips can be linearly aligned in the second direction at a shorter pitch.

In the above cell transfer device, it is preferable that the head unit includes a frame member for each of the heads, the frame member including a first frame portion which holds the head, and a second frame portion to which the first frame portion is attached and which is connected to a raising and lowering mechanism having the drive motor and is moved by the raising and lowering mechanism in the first direction, in which in a plan view from the first direction, the second frame portion has a first width in the second direction and the first frame portion has a second width smaller than the first width, and the frame member provided in each head has the same shape and is installed in the head unit such that the frame member of the head belonging to the first group and the frame member of the head belonging to the second group are opposed to each other and the first frame portions are adjacent to each other in the second direction.

According to the cell transfer device, the frame members of the first and second groups are installed in the head unit such that the second frame portion holds each drive motor on the one side or the other side in the third direction, while the first frame portions are adjacent to each other in the second direction. Accordingly, the above compact arrangement of the heads and the drive motors can be realized using the frame member. Additionally, the frame members of the first and second groups are arranged to be opposed to each other. Therefore, it is possible to allow the frame members of the first and second groups to have the same shape, thereby realizing cost reduction.

The cell transfer method according to another aspect of the present disclosure is a cell transfer method of transferring a cell suctioned by a tip to a predetermined position and discharging the cell, the method including the steps of preparing a microplate including a plurality of wells to which the cells are discharged, the wells being aligned at a first pitch in a predetermined direction, and the cell transfer device in which a plurality of heads are aligned such that the tip is aligned at a second pitch that is n-times the first pitch (n is an integer of 1 or more); mounting the microplate in a movable range of the head unit; moving the head unit to a mounting position of the microplate in a state where the cell is being suctioned by the tip of the head group; and simultaneously driving the plurality of drive motors to simultaneously move the plurality of heads in the first direction such that distal end openings of the plurality of tips enter the respective wells, and causing the plurality of tips to simultaneously discharge the cells.

According to the cell transfer method, the above cell transfer device is used which includes the tips aligned at the second pitch that is n-times the first pitch. Therefore, the distal end openings of the plurality of tips are allowed to simultaneously enter the wells of the microplate. Accordingly, the cells can be simultaneously discharged from the plurality of tips to enable efficient processing of cell transfer work.

The above cell transfer method preferably further includes the steps of preparing a dish in which a plurality of holding portions which hold the cells are aligned at a third pitch narrower than the first pitch in a predetermined direction; mounting the dish in a movable range of the head unit; moving the head unit to a mounting position of the dish in a state where the tip of the head group is empty; and driving one of the drive motors to move one of the heads in the first direction such that a distal end opening of one of the tips accesses the holding portion, and causing the tip to suction the cell and sequentially causing the other tips to conduct the suction in the same manner.

According to the cell transfer method, since the cells are suctioned by the tips from the dishes on a head basis, the dish not dependent on an alignment pitch of the tips can be used. Accordingly, a compact size dish can be used as the dish.

The present disclosure described above provides a cell transfer device in which a tip attached to a head mounted with a drive motor can be aligned at a required pitch, and a cell transfer method using the cell transfer device.

What is claimed is:

1. A cell transfer device comprising:
   a head group including a plurality of heads to which tips are attached and force driven for suctioning and discharging cells and which are configured to move along a first direction;
   a head unit includes the head group including the plurality of heads, and a head main body in which the head group is installed, and the head unit is configured to move in a second direction orthogonal to the first direction and in a third direction orthogonal to both the first direction and the second direction,
   wherein the first direction comprises an up-down direction, the second direction comprises a right-left direction, and the third direction comprises a front-rear-direction; and
   a plurality of drive motors which are mounted on the head unit so as to each correspond to each of the heads and which are configured to generate driving force to cause the head to move along the first direction,
   wherein the plurality of drive motors are separately arranged on one side and the other side of the head unit in the third direction with the head group provided therebetween in a plan view from the first direction,
   the head group includes at least a first head and a second head adjacent to the first head in the second direction, the first head being driven by the drive motor arranged on the one side in the third direction, and the second head being driven by the drive motor arranged on the other side in the third direction,
   wherein the plurality of heads provided in the head group are linearly aligned in the second direction and divided into heads belonging to a first group and heads belonging to a second group,
   the heads of the first group including the first head and being driven by each of the drive motors arranged on the one side in the third direction, and
   the heads of the second group including the second head and being driven by each of the drive motors arranged on the other side in the third direction.

2. The cell transfer device according to claim 1, further comprising:
   a plurality of suction motors which are mounted on the head unit so as to each correspond to each of the heads, and which are configured to generate driving force to cause the tips attached to the heads to suction and discharge the cells,
   wherein the suction motor arranged on the one side in the third direction is applied to the tip attached to the first head, and
   the suction motor arranged on the other side in the third direction is applied to the tip attached to the second head.

3. The cell transfer device according to claim 2, wherein the plurality of heads provided in the head group are linearly aligned in the second direction and divided into heads belonging to a first group and heads belonging to a second group,
   the heads of the first group including the first head and being driven by each of the drive motors arranged on the one side in the third direction,
   the heads of the second group including the second head and being driven by each of the drive motors arranged on the other side in the third direction,
   the suction motors applied to the tips attached to the respective heads of the first group are arranged on the one side in the third direction, and
   the suction motors applied to the tips attached to the respective heads of the second group are arranged on the other side in the third direction.

4. The cell transfer device according to claim 1, wherein
the plurality of heads are aligned in which the heads belonging to the first group and the heads belonging to the second group are arranged alternately, and in a plan view from the first direction, the drive motors arranged on the one side and the other side in the third direction are linearly aligned in the second direction on the one side and the other side, respectively.

5. The cell transfer device according to claim 4, wherein
the head unit includes a frame member for each of the heads, the frame member including a first frame portion configured to hold the head, and a second frame portion to which the first frame portion is attached and which is connected to a raising and lowering mechanism having the drive motor and is configured to move by the raising and lowering mechanism in the first direction, in a plan view from the first direction, the second frame portion has a first width in the second direction and the first frame portion has a second width smaller than the first width, and the frame member provided in each head has the same shape and is installed in the head unit such that the frame member of the head belonging to the first group and the frame member of the head belonging to the second group are opposed to each other and the first frame portions are adjacent to each other in the second direction.

6. The cell transfer device according to claim 2, wherein
the plurality of heads provided in the head group are linearly aligned in the second direction and divided into heads belonging to a first group and heads belonging to a second group, the heads of the first group including the first head and being driven by each of the drive motors arranged on the one side in the third direction, and the heads of the second group including the second head and being driven by each of the drive motors arranged on the other side in the third direction.

7. The cell transfer device according to claim 3, wherein
the plurality of heads are aligned in which the heads belonging to the first group and the heads belonging to the second group are arranged alternately, and in a plan view from the first direction, the drive motors arranged on the one side and the other side in the third direction are linearly aligned in the second direction on the one side and the other side, respectively.

* * * * *